(12) United States Patent
Gifford et al.

(10) Patent No.: US 11,041,839 B2
(45) Date of Patent: Jun. 22, 2021

(54) DISTRIBUTION SYSTEM MONITORING

(71) Applicant: Mueller International, LLC, Atlanta, GA (US)

(72) Inventors: Paul Gifford, Chattanooga, TN (US); Timofey Sitnikov, Harrison, TN (US); Harold Mosley, Ooltewah, TN (US)

(73) Assignee: Mueller International, LLC, Atlanta, GA (US)

( * ) Notice: Subject to any disclaimer, the term of this patent is extended or adjusted under 35 U.S.C. 154(b) by 0 days.

(21) Appl. No.: 15/171,722

(22) Filed: Jun. 2, 2016

(65) Prior Publication Data

US 2016/0356755 A1 Dec. 8, 2016

Related U.S. Application Data

(60) Provisional application No. 62/171,897, filed on Jun. 5, 2015.

(51) Int. Cl.
*G01N 33/18* (2006.01)
*G06Q 50/06* (2012.01)
(Continued)

(52) U.S. Cl.
CPC ........... *G01N 33/18* (2013.01); *G05D 7/0617* (2013.01); *G06Q 50/06* (2013.01)

(58) Field of Classification Search
CPC ............ C02F 2209/00; C02F 2209/003; E03C 1/057; F16K 31/046; G05D 7/0617; G06Q 50/56; G06Q 50/06
(Continued)

(56) References Cited

U.S. PATENT DOCUMENTS 1,661,265 A  3/1928 Olbricht
1,788,618 A  1/1931 Cover
(Continued)

FOREIGN PATENT DOCUMENTS

AU  2009308949  5/2010
AU  2010249499  5/2015
(Continued)

OTHER PUBLICATIONS

US 10,101,311 B2, 10/2018, Clark et al. (withdrawn)
(Continued)

*Primary Examiner* — Seth W. Mackay-Smith
(74) *Attorney, Agent, or Firm* — Taylor English Duma LLP

(57) ABSTRACT

A method of sensing parameters in a fluid distribution system includes the steps of receiving, at a monitoring device, fluid parameter information from a sensor in a fluid distribution system; collecting, by the monitoring device, sampling data of the fluid parameter information from the sensor based on predetermined criteria; receiving, by the monitoring device, a request to collect transient data from the sensor; collecting, by the monitoring device, transient data of the fluid parameter information from the sensor based on predetermined criteria; and communicating the sampling data and the transient data to another device. An apparatus includes a monitoring device including a power source, an antenna, and a parameter sensing portion configured to monitor a parameter of a fluid distribution system; and a sensor array connected to the monitoring device

19 Claims, 25 Drawing Sheets

(51) Int. Cl.
  *F16K 31/04* (2006.01)
  *G05D 7/06* (2006.01)

(58) Field of Classification Search
  USPC .................................................. 251/129.04
  See application file for complete search history.

(56) References Cited

U.S. PATENT DOCUMENTS

| | | | |
|---|---|---|---|
| 1,901,772 A | 3/1933 | Pfau | |
| 2,099,479 A * | 11/1937 | Heinkel | E03B 9/10 137/367 |
| 2,336,450 A | 12/1943 | Voorhess et al. | |
| 2,524,031 A | 10/1950 | Arps | |
| 2,828,762 A * | 4/1958 | Swank | E03B 9/10 137/371 |
| 2,931,383 A * | 4/1960 | Handley | F16K 31/5284 137/369 |
| 3,047,079 A | 7/1962 | Wepsala, Jr. | |
| 3,077,937 A | 2/1963 | Tirapolsky et al. | |
| 3,084,515 A | 4/1963 | Dougherty | |
| 3,128,998 A | 4/1964 | Sibley | |
| 3,391,735 A | 7/1968 | Schramm et al. | |
| 3,404,738 A | 10/1968 | Lindquist | |
| 3,602,603 A | 8/1971 | Fukasu et al. | |
| 3,705,385 A | 12/1972 | Batz | |
| 4,039,784 A | 8/1977 | Quarton | |
| 4,093,997 A | 6/1978 | Germer | |
| 4,120,031 A | 10/1978 | Kincheloe et al. | |
| 4,126,338 A | 11/1978 | Coel et al. | |
| 4,149,676 A | 4/1979 | Wieck | |
| 4,282,413 A | 8/1981 | Simons | |
| 4,291,375 A | 9/1981 | Wolf | |
| 4,388,690 A | 6/1983 | Lumsden | |
| 4,414,633 A | 11/1983 | Churchill | |
| 4,442,492 A | 4/1984 | Karlsson et al. | |
| 4,465,970 A | 8/1984 | Dimassimo et al. | |
| 4,491,186 A | 1/1985 | Alder | |
| 4,516,213 A | 5/1985 | Gidden | |
| 4,542,469 A | 9/1985 | Brandberry et al. | |
| 4,591,988 A | 5/1986 | Klima et al. | |
| 4,674,279 A | 6/1987 | Ali et al. | |
| 4,705,060 A | 11/1987 | Goulbourne | |
| 4,707,852 A | 11/1987 | Jahr et al. | |
| 4,727,900 A | 3/1988 | Dooling et al. | |
| 4,792,946 A | 12/1988 | Mayo | |
| 4,803,632 A | 2/1989 | Frew et al. | |
| 4,833,618 A | 5/1989 | Verma et al. | |
| 4,868,566 A | 9/1989 | Strobel et al. | |
| 4,881,070 A | 11/1989 | Burrowes et al. | |
| 4,940,976 A | 7/1990 | Gastouniotis et al. | |
| 4,945,344 A | 7/1990 | Farrell | |
| 4,989,830 A | 2/1991 | Ratnik | |
| 5,006,240 A | 4/1991 | Steffero, Sr. | |
| 5,056,107 A | 10/1991 | Johnson et al. | |
| 5,075,792 A | 12/1991 | Brown et al. | |
| 5,079,715 A | 1/1992 | Venkataraman et al. | |
| 5,095,705 A | 3/1992 | Daly | |
| 5,121,344 A | 6/1992 | Laage et al. | |
| 5,239,575 A | 8/1993 | White et al. | |
| 5,298,894 A | 3/1994 | Cerny et al. | |
| 5,327,925 A * | 7/1994 | Ortel | E03B 9/10 137/15.08 |
| 5,381,136 A | 1/1995 | Powers et al. | |
| 5,434,911 A | 7/1995 | Gray et al. | |
| 5,438,329 A | 8/1995 | Gastouniotis et al. | |
| 5,451,938 A | 9/1995 | Brennan, Jr. | |
| 5,459,459 A | 10/1995 | Lee, Jr. | |
| 5,481,259 A | 1/1996 | Bane | |
| 5,493,287 A | 2/1996 | Bane | |
| 5,525,898 A | 6/1996 | Lee et al. | |
| 5,553,094 A | 9/1996 | Johnson et al. | |
| 5,588,462 A | 12/1996 | McHugh | |
| 5,590,179 A | 12/1996 | Shincovich et al. | |
| 5,594,740 A | 1/1997 | Ladue | |
| 5,617,084 A | 4/1997 | Sears | |
| 5,631,554 A | 5/1997 | Briese et al. | |
| 5,634,488 A * | 6/1997 | Martin, Jr. | F16L 59/168 137/364 |
| 5,646,863 A | 7/1997 | Morton | |
| 5,654,692 A | 8/1997 | Baxter, Jr. et al. | |
| 5,673,252 A | 9/1997 | Johnson et al. | |
| 5,708,195 A | 1/1998 | Kurisu et al. | |
| 5,714,931 A | 2/1998 | Petite | |
| 5,748,104 A | 5/1998 | Argyroudis et al. | |
| 5,751,797 A | 5/1998 | Saadeh | |
| 5,754,101 A | 5/1998 | Tsunetomi et al. | |
| 5,757,357 A | 5/1998 | Grande et al. | |
| 5,801,643 A | 9/1998 | Williams et al. | |
| 5,815,086 A | 9/1998 | Ivie et al. | |
| 5,852,658 A | 12/1998 | Knight et al. | |
| 5,877,703 A | 3/1999 | Bloss et al. | |
| 5,892,758 A | 4/1999 | Argyroudis | |
| 5,901,738 A * | 5/1999 | Miller | E03B 9/02 137/272 |
| 5,907,491 A | 5/1999 | Canada et al. | |
| 5,924,051 A | 7/1999 | Provost et al. | |
| 5,926,103 A | 7/1999 | Petite | |
| 5,926,531 A | 7/1999 | Petite | |
| 5,940,009 A | 8/1999 | Loy et al. | |
| 5,963,146 A | 10/1999 | Johnson et al. | |
| 5,971,011 A | 10/1999 | Price | |
| 5,993,739 A * | 11/1999 | Lyon | B60S 3/04 134/108 |
| 5,994,892 A | 11/1999 | Turino et al. | |
| 6,006,212 A | 12/1999 | Schleich et al. | |
| 6,028,522 A | 2/2000 | Petite | |
| 6,031,455 A | 2/2000 | Grube et al. | |
| 6,036,401 A * | 3/2000 | Morina | E02D 29/1409 137/370 |
| 6,044,062 A | 3/2000 | Brownrigg et al. | |
| 6,058,374 A | 5/2000 | Guthrie et al. | |
| 6,060,994 A | 5/2000 | Chen | |
| 6,078,269 A | 6/2000 | Markwell | |
| 6,081,204 A | 6/2000 | Lavoie et al. | |
| 6,163,276 A | 12/2000 | Irving et al. | |
| 6,172,616 B1 | 1/2001 | Johnson et al. | |
| 6,194,902 B1 | 2/2001 | Kuo | |
| 6,195,018 B1 | 2/2001 | Ragle et al. | |
| 6,218,953 B1 | 4/2001 | Petite | |
| 6,233,327 B1 | 5/2001 | Petite | |
| 6,246,677 B1 | 6/2001 | Nap et al. | |
| 6,249,516 B1 | 6/2001 | Brownrigg et al. | |
| 6,288,641 B1 | 9/2001 | Casais | |
| 6,317,051 B1 | 11/2001 | Cohen | |
| 6,333,975 B1 | 12/2001 | Brunn et al. | |
| 6,356,205 B1 | 3/2002 | Salvo et al. | |
| 6,373,399 B1 | 4/2002 | Johnson et al. | |
| 6,392,538 B1 | 5/2002 | Shere | |
| 6,424,270 B1 | 7/2002 | Ali | |
| 6,430,268 B1 | 8/2002 | Petite | |
| 6,437,692 B1 | 8/2002 | Petite et al. | |
| 6,453,247 B1 | 9/2002 | Hunaidi | |
| 6,456,197 B1 | 9/2002 | Lauritsen et al. | |
| 6,470,903 B2 | 10/2002 | Reyman | |
| 6,487,457 B1 | 11/2002 | Hull et al. | |
| 6,493,377 B2 | 12/2002 | Schilling et al. | |
| 6,512,463 B1 | 1/2003 | Campbell et al. | |
| 6,528,957 B1 | 3/2003 | Luchaco | |
| 6,538,577 B1 | 3/2003 | Ehrke et al. | |
| 6,560,543 B2 | 5/2003 | Wolfe et al. | |
| 6,564,159 B1 | 5/2003 | Lavoie et al. | |
| 6,577,961 B1 | 6/2003 | Hubbard et al. | |
| 6,618,578 B1 | 9/2003 | Petite | |
| 6,624,750 B1 | 9/2003 | Marman et al. | |
| 6,628,207 B1 | 9/2003 | Hemminger et al. | |
| 6,628,764 B1 | 9/2003 | Petite | |
| 6,633,781 B1 | 10/2003 | Lee et al. | |
| 6,653,945 B2 | 11/2003 | Johnson et al. | |
| 6,657,552 B2 | 12/2003 | Belski et al. | |
| 6,675,071 B1 | 1/2004 | Griffin, Jr. et al. | |
| 6,675,834 B1 | 1/2004 | Lai | |
| 6,677,861 B1 | 1/2004 | Henry et al. | |
| 6,710,721 B1 | 3/2004 | Holowick | |

(56) References Cited

U.S. PATENT DOCUMENTS

| | | |
|---|---|---|
| 6,747,557 B1 | 6/2004 | Petite et al. |
| 6,798,352 B2 | 9/2004 | Holowick |
| 6,816,072 B2 | 11/2004 | Zoratti |
| 6,830,061 B2 | 12/2004 | Adams et al. |
| 6,836,737 B2 | 12/2004 | Petite et al. |
| 6,847,300 B2 | 1/2005 | Yee et al. |
| 6,876,100 B2 | 4/2005 | Yumita |
| 6,891,477 B2 | 5/2005 | Aronstam |
| 6,891,838 B1 | 5/2005 | Petite et al. |
| 6,912,472 B2 | 6/2005 | Mizushina et al. |
| 6,914,533 B2 | 7/2005 | Petite |
| 6,914,893 B2 | 7/2005 | Petite |
| 6,931,445 B2 | 8/2005 | Davis |
| 6,946,972 B2 | 9/2005 | Mueller et al. |
| 6,954,701 B2 | 10/2005 | Wolfe |
| 6,954,814 B1 | 10/2005 | Leach |
| 6,963,808 B1 | 11/2005 | Addink et al. |
| 6,963,817 B2 | 11/2005 | Ito et al. |
| 6,970,808 B2 | 11/2005 | Abhulimen et al. |
| 6,972,677 B2 | 12/2005 | Coulthard |
| 6,978,210 B1 | 12/2005 | Suter et al. |
| 6,980,079 B1 | 12/2005 | Shintani et al. |
| 6,998,724 B2 | 2/2006 | Johansen et al. |
| 7,002,481 B1 | 2/2006 | Crane et al. |
| 7,008,239 B1 | 3/2006 | Ju |
| 7,009,530 B2 | 3/2006 | Zigdon et al. |
| 7,012,546 B1 | 3/2006 | Zigdon et al. |
| 7,020,701 B1 | 3/2006 | Gelvin et al. |
| 7,042,368 B2 | 5/2006 | Patterson et al. |
| 7,053,767 B2 | 5/2006 | Petite et al. |
| 7,054,271 B2 | 5/2006 | Brownrigg |
| 7,061,924 B1 | 6/2006 | Durrant et al. |
| 7,072,945 B1 | 7/2006 | Nieminen et al. |
| 7,079,810 B2 | 7/2006 | Petite et al. |
| 7,088,239 B2 | 8/2006 | Basinger et al. |
| 7,089,125 B2 | 8/2006 | Sonderegger |
| 7,103,511 B2 | 9/2006 | Petite |
| 7,117,051 B2 | 10/2006 | Landry et al. |
| 7,124,184 B2 | 10/2006 | Chung et al. |
| 7,137,550 B1 | 11/2006 | Petite |
| 7,142,107 B2 | 11/2006 | Kates |
| 7,201,180 B2 | 4/2007 | Ephrat et al. |
| 7,219,553 B1 | 5/2007 | Worthington |
| 7,248,181 B2 | 7/2007 | Patterson et al. |
| 7,252,431 B1 | 8/2007 | Caramanna |
| 7,253,536 B2 | 8/2007 | Fujimoto et al. |
| 7,256,704 B2 | 8/2007 | Yoon et al. |
| 7,263,073 B2 | 8/2007 | Petite et al. |
| 7,290,450 B2 | 11/2007 | Brown et al. |
| 7,292,143 B2 | 11/2007 | Drake et al. |
| 7,295,128 B2 | 11/2007 | Petite |
| 7,301,456 B2 | 11/2007 | Han |
| 7,310,590 B1 | 12/2007 | Bansal et al. |
| 7,315,257 B2 | 1/2008 | Patterson et al. |
| 7,330,796 B2 | 2/2008 | Addink et al. |
| 7,342,504 B2 | 3/2008 | Crane et al. |
| 7,353,280 B2 | 4/2008 | Chiles et al. |
| 7,356,614 B2 | 4/2008 | Kim et al. |
| 7,363,031 B1 | 4/2008 | Aisa |
| 7,397,907 B2 | 7/2008 | Petite |
| 7,412,882 B2 | 8/2008 | Lazar et al. |
| 7,417,557 B2 | 8/2008 | Osterloh et al. |
| 7,423,985 B1 | 9/2008 | Hill |
| 7,424,527 B2 | 9/2008 | Petite |
| 7,443,313 B2 | 10/2008 | Davis et al. |
| 7,444,401 B1 | 10/2008 | Keyghobad |
| 7,453,373 B2 | 11/2008 | Cumeralto et al. |
| 7,468,661 B2 | 12/2008 | Petite et al. |
| 7,478,108 B2 | 1/2009 | Townsend et al. |
| 7,480,501 B2 | 1/2009 | Petite |
| 7,497,957 B2 | 3/2009 | Bernard |
| 7,523,016 B1 | 4/2009 | Surdulescu et al. |
| 7,526,539 B1 | 4/2009 | Hsu |
| 7,550,746 B2 * | 6/2009 | Tokhtuev ............ G01N 21/6402 250/461.1 |
| 7,650,425 B2 | 1/2010 | Davis |
| 7,696,940 B1 | 4/2010 | MacDonald |
| 7,697,492 B2 | 4/2010 | Petite |
| 7,739,378 B2 | 6/2010 | Petite |
| 7,752,309 B2 | 7/2010 | Keyghobad et al. |
| 7,756,086 B2 | 7/2010 | Petite |
| 7,767,093 B2 | 8/2010 | Frank |
| 7,783,738 B2 | 8/2010 | Keyghobad et al. |
| 7,792,946 B2 | 9/2010 | Keyghobad et al. |
| 7,870,080 B2 | 1/2011 | Budike, Jr. |
| 7,880,641 B2 * | 2/2011 | Parris ................ G01D 4/002 137/625.11 |
| 7,920,983 B1 | 4/2011 | Peleg |
| 7,980,317 B1 | 7/2011 | Preta et al. |
| 8,082,945 B1 * | 12/2011 | White ................ F16K 27/006 137/369 |
| 8,109,131 B2 | 2/2012 | Winter |
| 8,140,667 B2 | 3/2012 | Keyghobad et al. |
| 8,249,042 B2 | 8/2012 | Sparr et al. |
| 8,341,106 B1 | 12/2012 | Scolnicov et al. |
| 8,351,409 B2 | 1/2013 | Albert et al. |
| 8,360,720 B2 | 1/2013 | Schlabach et al. |
| 8,407,333 B2 | 3/2013 | Keyghobad et al. |
| 8,423,637 B2 | 4/2013 | Vaswani et al. |
| 8,549,131 B2 | 10/2013 | Keyghobad |
| 8,583,386 B2 | 11/2013 | Armon et al. |
| 8,615,374 B1 | 12/2013 | Discenzo |
| 8,823,509 B2 | 9/2014 | Hyland et al. |
| 8,931,505 B2 | 1/2015 | Hyland et al. |
| 9,053,519 B2 | 6/2015 | Scolnicov et al. |
| 9,104,189 B2 | 8/2015 | Berges Gonzalez et al. |
| 9,134,204 B2 | 9/2015 | Mohajer |
| 9,202,362 B2 | 12/2015 | Hyland et al. |
| 9,441,988 B2 | 9/2016 | Armon et al. |
| 9,568,391 B2 | 2/2017 | Linford et al. |
| 9,568,392 B2 | 2/2017 | Peleg et al. |
| 9,583,386 B2 | 2/2017 | Kolics et al. |
| 9,588,094 B2 | 3/2017 | Wolfe |
| 9,604,858 B2 * | 3/2017 | Kamen ................ C02F 1/041 |
| 9,749,792 B2 | 8/2017 | Klicpera |
| 9,760,097 B2 | 9/2017 | Masias et al. |
| 9,777,457 B2 * | 10/2017 | Mosley ................ E03B 9/10 |
| 9,799,204 B2 * | 10/2017 | Hyland ................ H04Q 9/00 |
| 9,822,519 B2 | 11/2017 | Hall et al. |
| 9,863,425 B2 | 1/2018 | Kallesoe et al. |
| 9,934,670 B2 | 4/2018 | Hyland et al. |
| 9,952,605 B2 | 4/2018 | Griffin, Jr. et al. |
| 10,030,818 B2 | 7/2018 | Hoskins et al. |
| 10,180,414 B2 | 1/2019 | Clark et al. |
| 10,193,778 B2 | 1/2019 | Vaswani et al. |
| 10,203,315 B2 | 2/2019 | Clark et al. |
| 10,242,414 B2 | 3/2019 | Scolnicov et al. |
| 10,262,518 B2 | 4/2019 | Hyland et al. |
| 10,402,044 B2 | 9/2019 | Rose et al. |
| 10,410,501 B2 | 9/2019 | Klicpera |
| 10,489,038 B2 | 11/2019 | Klicpera |
| 10,564,802 B2 | 2/2020 | Rose et al. |
| 10,571,358 B2 | 2/2020 | Campan et al. |
| 10,837,858 B2 | 11/2020 | Seddiq et al. |
| 2001/0010032 A1 | 7/2001 | Ehlers et al. |
| 2001/0013488 A1 | 8/2001 | Fukunaga et al. |
| 2001/0024163 A1 | 9/2001 | Petite |
| 2001/0048030 A1 | 12/2001 | Sharood et al. |
| 2002/0002425 A1 * | 1/2002 | Dossey ................ G01F 1/44 700/284 |
| 2002/0013679 A1 | 1/2002 | Petite |
| 2002/0019725 A1 | 2/2002 | Petite |
| 2002/0031101 A1 | 3/2002 | Petite |
| 2002/0043969 A1 | 4/2002 | Duncan |
| 2002/0062392 A1 | 5/2002 | Nishikawa et al. |
| 2002/0067717 A1 | 6/2002 | Raschke et al. |
| 2002/0073183 A1 | 6/2002 | Yoon et al. |
| 2002/0077777 A1 | 6/2002 | Wolfe et al. |
| 2002/0089802 A1 | 7/2002 | Beckwith |
| 2002/0105346 A1 | 8/2002 | Banks |
| 2002/0130069 A1 | 9/2002 | Moskoff |
| 2002/0130768 A1 | 9/2002 | Che et al. |
| 2002/0149487 A1 | 10/2002 | Haines |
| 2002/0169643 A1 | 11/2002 | Petite et al. |

(56) References Cited

U.S. PATENT DOCUMENTS

| | | |
|---|---|---|
| 2002/0190956 A1 | 12/2002 | Klein et al. |
| 2003/0009515 A1 | 1/2003 | Lee et al. |
| 2003/0018733 A1 | 1/2003 | Yoon et al. |
| 2003/0018776 A1 | 1/2003 | Yoon et al. |
| 2003/0036810 A1 | 2/2003 | Petite |
| 2003/0046377 A1 | 3/2003 | Daum et al. |
| 2003/0074109 A1 | 4/2003 | Jeong et al. |
| 2003/0093484 A1 | 5/2003 | Petite |
| 2003/0107485 A1* | 6/2003 | Zoratti ............... E03B 9/04 340/568.1 |
| 2003/0174070 A1 | 9/2003 | Garrod et al. |
| 2004/0006513 A1 | 1/2004 | Wolfe |
| 2004/0010561 A1 | 1/2004 | Kim |
| 2004/0054747 A1 | 3/2004 | Breh |
| 2004/0064217 A1* | 4/2004 | Addink ............... A01G 25/16 700/284 |
| 2001/0138840 | 7/2004 | Wolfe |
| 2004/0129312 A1 | 7/2004 | Cuzzo et al. |
| 2004/0138840 A1 | 7/2004 | Wolfe |
| 2004/0139210 A1 | 7/2004 | Lee et al. |
| 2004/0154965 A1* | 8/2004 | Baum ............... C02F 1/008 210/85 |
| 2004/0158333 A1 | 8/2004 | Ha et al. |
| 2004/0159149 A1 | 8/2004 | Williams et al. |
| 2004/0183687 A1 | 9/2004 | Petite et al. |
| 2004/0199340 A1 | 10/2004 | Kersey et al. |
| 2004/0212510 A1 | 10/2004 | Aronstam |
| 2004/0237545 A1 | 12/2004 | Tanaka et al. |
| 2005/0009192 A1* | 1/2005 | Page ............... C02F 1/006 436/55 |
| 2005/0072214 A1 | 4/2005 | Cooper |
| 2005/0084418 A1 | 4/2005 | Hill et al. |
| 2005/0096753 A1 | 5/2005 | Arling |
| 2005/0104747 A1 | 5/2005 | Silic et al. |
| 2005/0120778 A1 | 6/2005 | Von Herzen et al. |
| 2005/0159823 A1 | 7/2005 | Hayes |
| 2005/0195768 A1 | 9/2005 | Petite et al. |
| 2005/0195775 A1 | 9/2005 | Petite et al. |
| 2005/0201379 A1 | 9/2005 | Zhang et al. |
| 2005/0201397 A1 | 9/2005 | Petite |
| 2005/0203647 A1 | 9/2005 | Landry et al. |
| 2005/0247114 A1 | 11/2005 | Kahn |
| 2005/0251366 A1 | 11/2005 | Kahn et al. |
| 2005/0251367 A1 | 11/2005 | Kahn et al. |
| 2005/0279169 A1 | 12/2005 | Lander |
| 2006/0028355 A1 | 2/2006 | Patterson et al. |
| 2006/0031040 A1 | 2/2006 | Wolfe |
| 2006/0041655 A1 | 2/2006 | Holloway et al. |
| 2006/0272830 A1 | 2/2006 | Fima |
| 2006/0046664 A1 | 3/2006 | Paradiso et al. |
| 2006/0059977 A1 | 3/2006 | Kates |
| 2006/0098576 A1 | 5/2006 | Brownrigg et al. |
| 2006/0122736 A1 | 6/2006 | Alexanian |
| 2006/0158347 A1 | 7/2006 | Roche et al. |
| 2006/0174707 A1 | 8/2006 | Zhang |
| 2006/0181414 A1 | 8/2006 | Bandy et al. |
| 2006/0197345 A1 | 9/2006 | Kuroki et al. |
| 2006/0201550 A1 | 9/2006 | Blyth et al. |
| 2006/0218266 A1 | 9/2006 | Matsumoto et al. |
| 2006/0248961 A1 | 11/2006 | Shachar |
| 2006/0273896 A1 | 12/2006 | Kates |
| 2007/0035315 A1 | 2/2007 | Hilleary |
| 2007/0050157 A1 | 3/2007 | Kahn et al. |
| 2007/0052540 A1 | 3/2007 | Hall et al. |
| 2007/0059986 A1 | 3/2007 | Rockwell |
| 2007/0063866 A1 | 3/2007 | Webb |
| 2007/0090059 A1 | 4/2007 | Plummer |
| 2007/0163965 A1 | 7/2007 | Wolfe |
| 2007/0219728 A1 | 9/2007 | Papageorgiou et al. |
| 2007/0293990 A1* | 12/2007 | Alexanain ............... A01G 25/16 700/284 |
| 2007/0298779 A1 | 12/2007 | Wolman et al. |
| 2008/0023077 A1* | 1/2008 | Weisz ............... B25B 13/48 137/370 |
| 2008/0030319 A1 | 2/2008 | McKeena et al. |
| 2008/0095403 A1 | 4/2008 | Benhammou |
| 2008/0109090 A1 | 5/2008 | Esmaili et al. |
| 2008/0109175 A1 | 5/2008 | Michalak |
| 2008/0122641 A1 | 5/2008 | Amidi |
| 2008/0136191 A1 | 6/2008 | Baarman et al. |
| 2008/0149180 A1* | 6/2008 | Parris ............... E03B 7/072 137/1 |
| 2008/0155064 A1 | 6/2008 | Kosuge |
| 2008/0186898 A1 | 8/2008 | Petite |
| 2008/0195329 A1 | 8/2008 | Prince et al. |
| 2008/0289402 A1 | 11/2008 | Chowdhury |
| 2008/0291054 A1 | 11/2008 | Groft |
| 2009/0040057 A1 | 2/2009 | Keyghobad |
| 2009/0044628 A1 | 2/2009 | Lotscher |
| 2009/0066524 A1 | 3/2009 | Yukawa et al. |
| 2009/0068947 A1 | 3/2009 | Petite |
| 2009/0084734 A1* | 4/2009 | Yencho ............... C02F 1/325 210/741 |
| 2009/0099701 A1 | 4/2009 | Li et al. |
| 2009/0121860 A1 | 5/2009 | Kimmel et al. |
| 2009/0123340 A1 | 5/2009 | Knudsen et al. |
| 2009/0125241 A1 | 5/2009 | Frank |
| 2009/0157521 A1 | 6/2009 | Moren |
| 2009/0204265 A1 | 8/2009 | Hackett |
| 2009/0215424 A1 | 8/2009 | Petite |
| 2009/0243840 A1 | 10/2009 | Petite et al. |
| 2009/0260697 A1 | 10/2009 | Mevius et al. |
| 2009/0271045 A1 | 10/2009 | Savelle |
| 2009/0281677 A1 | 11/2009 | Botich et al. |
| 2009/0287838 A1 | 11/2009 | Keyghobad et al. |
| 2009/0287966 A1 | 11/2009 | Keyghobad |
| 2009/0301571 A1 | 12/2009 | Ruhs |
| 2009/0309755 A1 | 12/2009 | Williamson |
| 2009/0319853 A1 | 12/2009 | Keyghobad |
| 2010/0017465 A1 | 1/2010 | Brownrigg et al. |
| 2010/0039984 A1 | 2/2010 | Brownrigg |
| 2010/0085211 A1 | 4/2010 | Wang et al. |
| 2010/0105146 A1 | 4/2010 | Meeusen |
| 2010/0156632 A1 | 6/2010 | Hyland et al. |
| 2010/0193430 A1* | 8/2010 | Whiteman ............... C02F 3/006 210/610 |
| 2010/0194582 A1 | 8/2010 | Petite |
| 2010/0204924 A1 | 8/2010 | Wolfe et al. |
| 2010/0214120 A1 | 8/2010 | Means |
| 2010/0250054 A1 | 9/2010 | Petite |
| 2010/0265909 A1 | 10/2010 | Petite et al. |
| 2010/0295672 A1 | 11/2010 | Hyland et al. |
| 2010/0312881 A1 | 12/2010 | Davis et al. |
| 2010/0313958 A1 | 12/2010 | Patel et al. |
| 2010/0332149 A1* | 12/2010 | Scholpp ............... C02F 1/008 702/25 |
| 2011/0030482 A1 | 2/2011 | Meeusen et al. |
| 2011/0044276 A1 | 2/2011 | Albert et al. |
| 2011/0059462 A1* | 3/2011 | Lim ............... G01N 1/4077 435/6.13 |
| 2011/0079402 A1 | 4/2011 | Darby et al. |
| 2011/0093123 A1 | 4/2011 | Alexanian |
| 2011/0111700 A1 | 5/2011 | Hackett |
| 2011/0125412 A1 | 5/2011 | Salzer et al. |
| 2011/0132484 A1 | 6/2011 | Teach et al. |
| 2011/0178644 A1 | 7/2011 | Picton |
| 2011/0190947 A1 | 8/2011 | Savelle, Jr. et al. |
| 2011/0215945 A1 | 9/2011 | Peleg et al. |
| 2011/0233935 A1 | 9/2011 | Baarman et al. |
| 2011/0257788 A1* | 10/2011 | Wiemers ............... B01D 61/022 700/267 |
| 2011/0307203 A1* | 12/2011 | Higgins ............... G05B 15/02 702/84 |
| 2011/0308638 A1* | 12/2011 | Hyland ............... F17D 5/02 137/299 |
| 2012/0007744 A1 | 1/2012 | Pal et al. |
| 2012/0016823 A1 | 1/2012 | Paillet et al. |
| 2012/0025997 A1 | 2/2012 | Liu et al. |
| 2012/0038170 A1 | 2/2012 | Stuart et al. |
| 2012/0048386 A1 | 3/2012 | Clark |
| 2012/0106518 A1 | 5/2012 | Albert et al. |
| 2012/0116827 A1 | 5/2012 | Susumago |

(56) References Cited

U.S. PATENT DOCUMENTS

| | | |
|---|---|---|
| 2012/0118397 A1 | 5/2012 | Novotny et al. |
| 2012/0121386 A1 | 5/2012 | Dahlhaug |
| 2012/0132445 A1 | 5/2012 | Mallon et al. |
| 2012/0191868 A1 | 7/2012 | Keyghobad |
| 2012/0206258 A1 | 8/2012 | Ramesh |
| 2012/0271686 A1 | 10/2012 | Silverman |
| 2012/0298208 A1 | 11/2012 | Taylor et al. |
| 2012/0298381 A1 | 11/2012 | Taylor |
| 2012/0311170 A1 | 12/2012 | Keyghobad et al. |
| 2013/0029683 A1 | 1/2013 | Kim et al. |
| 2013/0036800 A1 | 2/2013 | Mohajer |
| 2013/0041601 A1 | 2/2013 | Dintakurti et al. |
| 2013/0118239 A1 | 5/2013 | Forstmeier |
| 2013/0168327 A1 | 7/2013 | Clark |
| 2013/0170417 A1 | 7/2013 | Thomas et al. |
| 2013/0211797 A1 | 8/2013 | Scolnicov |
| 2013/0317659 A1 | 11/2013 | Thomas et al. |
| 2013/0332090 A1 | 12/2013 | Scolnicov et al. |
| 2013/0341934 A1 | 12/2013 | Kawanishi |
| 2014/0026644 A1 | 1/2014 | Patel et al. |
| 2014/0262998 A1 | 6/2014 | Wagner et al. |
| 2014/0224026 A1 | 8/2014 | Linford et al. |
| 2014/0278246 A1 | 9/2014 | Clark et al. |
| 2014/0340238 A1 | 11/2014 | Hyland |
| 2015/0198057 A1 | 7/2015 | Hanna |
| 2015/0308627 A1 | 10/2015 | Hoskins |
| 2015/0327449 A1* | 11/2015 | Bartlett ............... A01G 25/167 137/15.08 |
| 2016/0049067 A1 | 2/2016 | Hyland |
| 2016/0163177 A1 | 6/2016 | Klicpera |
| 2017/0059543 A1 | 3/2017 | Clark |
| 2017/0367578 A1 | 12/2017 | Melodia et al. |
| 2018/0174424 A1 | 6/2018 | Hyland et al. |
| 2018/0372706 A1 | 12/2018 | Clark et al. |
| 2018/0372707 A1 | 12/2018 | Clark et al. |
| 2018/0372708 A1 | 12/2018 | Clark et al. |

FOREIGN PATENT DOCUMENTS

| | | |
|---|---|---|
| AU | 2014259545 | 11/2015 |
| AU | 2015202223 | 9/2016 |
| AU | 2014235054 | 2/2018 |
| AU | 2018200410 | 1/2019 |
| AU | 2018253559 | 11/2020 |
| CA | 2634759 | 12/2009 |
| CA | 2650174 | 7/2012 |
| CA | 2741843 | 5/2018 |
| CA | 2772545 | 12/2018 |
| CA | 2978661 | 4/2021 |
| CN | 1185838 | 6/1998 |
| CN | 1458405 | 11/2003 |
| CN | 2630512 | 8/2004 |
| CN | 101871834 | 10/2010 |
| CN | 102095837 | 6/2011 |
| CN | 204828756 | 12/2015 |
| DE | 4124154 | 1/1993 |
| DE | 19757581 | 7/1998 |
| DE | 202006017758 | 2/2007 |
| EP | 1901253 | 3/2008 |
| EP | 2433440 | 7/2018 |
| EP | 2350992 | 1/2019 |
| EP | 3422319 | 1/2019 |
| EP | 3422320 | 1/2019 |
| GB | 2305333 | 4/1997 |
| GB | 2401406 | 11/2004 |
| GB | 2507184 | 4/2014 |
| JP | 62-295674 | 12/1987 |
| JP | 05-253316 | 10/1993 |
| JP | 06-223279 | 8/1994 |
| JP | 6300606 | 10/1994 |
| JP | H0731989 | 2/1995 |
| JP | 07-116285 | 5/1995 |
| JP | 07231363 | 8/1995 |
| JP | 2008128079 | 5/1996 |
| JP | 11-046254 | 2/1999 |
| JP | 2000285356 | 10/2000 |
| JP | 2001200952 | 7/2001 |
| JP | 2001254662 | 9/2001 |
| JP | 2002352361 | 12/2002 |
| JP | 2003172243 | 6/2003 |
| JP | 2006285645 | 10/2006 |
| JP | 2008198044 | 8/2008 |
| JP | 2012507090 | 3/2012 |
| JP | 2012527706 | 11/2012 |
| JP | 2013200031 | 10/2013 |
| KR | 20110092242 | 8/2011 |
| WO | 9810299 | 3/1998 |
| WO | 9810394 | 3/1998 |
| WO | 03067021 | 8/2003 |
| WO | 2008087911 | 7/2008 |
| WO | 2009012254 | 1/2009 |
| WO | 2009100476 | 8/2009 |
| WO | 2010051287 | 5/2010 |
| WO | 2010099348 | 9/2010 |
| WO | 2010135587 | 11/2010 |
| WO | 2012069688 | 5/2012 |
| WO | 2012099588 | 7/2012 |
| WO | 2014151384 | 9/2014 |
| WO | 2016197096 | 12/2016 |

OTHER PUBLICATIONS

Vonroll Hydro—Hydrojournal, pp. 1-16, May 2008.
English Translation: Vonroll Hydro—Hyrdojournal, Technology with a Future for Shut-off Systems—p. 4, VonRoll Hydro (shop) GmbH—New Concepts for Apprentice Training—p. 12, May 2008.
Von Roll Hydro—Hydrojournal, pp. 1-16, Nov. 2008.
English Translation: Von Roll Hydro—Hyrdojournal, VonRoll Hydroalert—Provides a Warning in the Event of Any Tampering with the Water Supply, p. 3, Nov. 2008.
Keyghobad, Seyamak; Examiner Interview Summary Record for U.S. Appl. No. 10/298,300, filed Nov. 18, 2002; dated Feb. 5, 2008; 2 pages.
Keyghobad, Seyamak; Non-Final Rejection for U.S. Appl. No. 10/298,300, filed Nov. 18, 2002; dated Oct. 26, 2007; 35 pages.
Keyghobad, Seyamak; Requirement for Restriction/ Election for U.S. Appl. No. 10/298,300, filed Nov. 18, 2002; dated Feb. 27, 2006; 17 pages.
Keyghobad, Seyamak; Non-Final Rejection for U.S. Appl. No. 10/298,300, filed Nov. 18, 2002; dated May 18, 2006; 13 pages.
Keyghobad, Seyamak; Non-Final Rejection or U.S. Appl. No. 10/298,300, filed Nov. 18, 2002; dated Jun. 6, 2007; 32 pages.
Keyghobad, Seyamak; Certificate of Correction for U.S. Appl. No. 10/298,300, filed Nov. 18, 2002; dated Mar. 31, 2009; 1 page.
Keyghobad, Seyamak; Notice of Allowance for U.S. Appl. No. 10/298,300, filed Nov. 18, 2002; dated Jul. 14, 2008; 4 pages.
Gifford, Paul; PCT Application entitled: Distribution System Monitoring, having serial No. PCT/US16/36007, filed Jun. 6, 2016, 53 pgs.
Gifford, Paul; U.S. Provisional Patent Application entitled: Distribution System Monitoring having U.S. Appl. No. 62/171,897, filed Jun. 5, 2015, 42 pgs.
Hyland, Gregory E.; Non-final Office Action for Continuation U.S. Appl. No. 14/928,725, filed Oct. 30, 2015, dated Jan. 25, 2017, 137 pgs.
Hyland, Gregory E.; Non-final Office Action for U.S. Appl. No. 14/450,452, filed Aug. 4, 2014, dated Feb. 2, 2017, 40 pgs.
Clark, Kenneth A.; Non-final Office Action for U.S. Appl. No. 14/209,257, filed Mar. 13, 2014, dated Feb. 22, 2017, 95 pgs.
Keyghobad, Seyamak; Notice of Allowance for U.S. Appl. No. 12/243,452, filed Oct. 1, 2008; dated Mar. 22, 2010; 8 pages.
Keyghobad, Seyamak; Examiner Interview Summary Record for U.S. Appl. No. 12/243,452, filed Oct. 1, 2008; dated Dec. 7, 2009; 3 pages.
Keyghobad, Seyamak; Non-Final Rejection for U.S. Appl. No. 12/243,452, filed Oct. 1, 2008; dated Sep. 14, 2009; 8 pages.
Keyghobad, Seyamak; Non-Final Rejection for U.S. Appl. No. 12/243,452, filed Oct. 1, 2008; dated May 1, 2009; 5 pages.

(56) References Cited

OTHER PUBLICATIONS

Keyghobad, Seyamak; Notice of Allowance for U.S. Appl. No. 12/490,925, filed Jun. 24, 2009; dated Jul. 19, 2010; 8 pages.
Keyghobad, Seyamak; Notice of Allowance for U.S. Appl. No. 12/490,925, filed Jun. 24, 2009; dated Jun. 28, 2010; 10 pgs.
Keyghobad, Seyamak; Notice of Allowance for U.S. Appl. No. 12/490,957, filed Jun. 24, 2009; dated Jun. 24, 2010; 10 pgs.
Keyghobad,Seyamak; Non-Final Rejection for U.S. Appl. No. 12/490,957, filed Jun. 24, 2009; dated Dec. 23, 2009; 8 pgs.
Young et al. "Real-Time Intranet-Controlled Virtual Instrument Multiple-Circuit Power Monitoring," IEEE Transactions on Instrumentation and Measurement, Jun. 2000. vol. 49, No. 3, p. 570. [Accessed Dec. 29, 2011] http://ieeexplore.ieee.org/xpls/abs_all.jsp, 6 pgs.
De Almeida et al. "Advanced Monitoring Technologies for the Evaluation of Demand-Side Management Programs," IEEE Transactions on Power Systems, Aug. 1994. vol. 9, No. 3. [Accessed Dec. 29, 2011] http://ieeexplore.ieee.org/xpls/abs_all.jsp?arnumber=336086, 7 pgs.
Dolezilek. "Microprocessor Based Relay Information Improves the Power System," Rural Electric Power Conference, May 1999. p. B5/1-B5/9. [Accessed Dec. 29, 2011] http://ieeexplore.ieee.org/xpls/abs_all.jsp?arnumber=768685, 9 pgs.
Gehami et al. "Electronic Control System | Salient Feature in Substation," Transmission & Distrubition, Mar. 1991. vol. 43, No. 3, p. 48. [Accessed Dec. 29, 2011—ProQuest].
Horlent. "New Metering and Reading Techniques Based on a Modular Design Concept," 10th International Conference on Electricity Distribution, May 1989. vol. 5, p. 455-459. [Accessed Dec. 29, 2011—IEEExplore].
"In Brief," Land Mobile Radio News, Jan. 16, 1998. vol. 52, No. 3, p. 1. [Accessed Dec. 29, 2011—ProQuest] http://proquest.umi.com/pqdweb?did=25435781&sid=1&Fmt=3&clientId=31810&RQT=309&VName%20=PQD.
"Landis & Gyr Utilities: Service Partnership Helps Utilities Use Available Resources More Effectively," www.landisgyr.com/utilities/e/fr_press1_e.htm (archived Feb. 6, 1998) http://web.archive.org/web/19980206060801/http://www.landisgyr.com/utilities.
Tamarkin. "Automated Meter Reading", Sep.-Oct. 1992, vol. 50, No. 5/ [Accessed Dec. 29, 2011] http://www.usclcorp.com/news/Automatic.
ANSI; "Protocol Specification for ANSI Type 2 Optical Port", American National Standard, ANSI C.12.18-2006, 11 pgs.
Federal Communications Commission; "Understanding the FCC Regulations for Low-Power, Non-Licensed Transmitters", Office of Engineering and Technology; Oct. 1993; 34 pgs.
Semtech; "TN1200.4, Calculating Radiated Power and Field Strength for Conducted Power Measurements", Semtech Corporation, Camarillo, CA, 2007, 9 pgs.
RFM; "HX 2000 Datasheet: 916.5 MHz: Hybrid Transmitter", RF Monolithics, Inc., Dallas, TX, USA, 1998; 2 pgs.
General Electric; "GEH-5081 kV Meter Product Manual", Nov. 1997, 137 pgs.
General Electric; "kV RSX—R5232/RS485 Communications Options: Instructions Manual"; Mar. 1999, 33 pgs.
Orfield; "Badger® ORION® System Helps Lemmon, South Dakota Reduce Read Time, Billing Cycles", Badger Connect Publication, 2004, 2 pgs.
AMCO; "Pit Water-Meter Transponder (PWT)"; AMCO Automated Systems, LLC; PDB-14611; Sep. 2002; 2 pgs.
AMCO; "Short-Range Programmer (SRP) VRT"; AMCO Automated Systems, LLC; PDB-14555.1; Sep. 2002; 2 pgs.
AMCO; Remote Water-Meter Transponder (RWT); AMCO Automated Systems, LLC; PDB-14610; Sep. 2002; 2 pgs.
Article entitled: "Remote Meter Reading", http://www.meter.co.uk/RMR.html; accessed on Jul. 30, 2012, 2 pgs.
Hyland, Gregory E.; Decision of Rejection for Japanese serial No. 2011-533427, filed Oct. 27, 2009, dated Sep. 16, 2014, 4 pgs.
Article entitled: "OET Exhibits List", https://apps.fcc.gov/oetcf/eas/reports/ViewExhibitReport.cfm?mode=Exhibits&RequestTimeout=500&calledFromFrame=N&application_id=194044&fcc_id=; Feb. 20, 2001, 2 pgs.
Patterson, Tim; Request for Ex Parte Reexamination under U.S. Appl. No. 90/012,468, filed Sep. 6, 2012; 52 pgs.
Patterson, Tim; Request for Ex Parte Reexamination under U.S. Appl. No. 90/012,449, filed Aug. 23, 2012; 51 pgs.
Radix Corporation; "Automatic Meter Reading", 2 pgs.
Trace; "Pit Water-Meter Transponder"; User Guide; Jan. 2003 16 pgs.
Hyland; European Search Report for serial No. EP09824079.9, filed Oct. 27, 2009, dated May 8, 2012; 38 pages.
Hyland, Gregory; Australian Patent Examination Report for serial No. 2009308949, filed Oct. 27, 2009, dated Nov. 12, 2013, 3 pgs.
Hyland, Gregory E.;Japanese Office Action for serial No. 2011-533427, filed Oct. 27, 2009, dated Apr. 30, 2013, 15 pgs.
Hyland, Gregory E.; Japanese Office Action for serial No. 2011-533427, filed Oct. 27, 2009, dated Feb. 4, 2014, 50 pgs.
Hyland, Gregory E.; Applicant Initiated Interview Summary for U.S. Appl. No. 12/606,957, filed Oct. 27, 2009, dated Feb. 18, 2014, 4 pgs.
Hyland, Gregory E.; Final Office Action for U.S. Appl. No. 12/606,957, filed Oct. 27, 2009, dated Dec. 17, 2013, 54 pgs.
Hyland, Gregory E.; Final Office Action for U.S. Appl. No. 12/606,957, filed Oct. 27, 2009, dated Apr. 10, 2013, 80 pgs.
Hyland, Gregory E.; Final Office Action for U.S. Appl. No. 12/606,957, filed Oct. 27, 2009, dated Sep. 22, 2014, 49 pgs.
Hyland, Gregory E.; Issue Notification for U.S. Appl. No. 12/606,957, filed Oct. 27, 2009, dated Nov. 11, 2015, 1 pg.
Hyland, Gregory E.; Non-Final Office Action for U.S. Appl. No. 12/606,957, filed Oct. 27, 2009, dated Oct. 18, 2012; 44 pgs.
Gregory E.; Non-Final Office Action for U.S. Appl. No. 12/606,957, filed Oct. 27, 2009, dated Apr. 8, 2014, 43 pgs.
Gregory E.; Non-Final Office Action for U.S. Appl. No. 12/606,957, filed Oct. 27, 2009, dated Sep. 6, 2013; 53 pgs.
Hyland, Gregory E.; Non-Final Office Action for U.S. Appl. No. 12/606,957, filed Oct. 27, 2009, dated Apr. 16, 2015, 47 pgs.
Hyland, Gregory E.; Notice of Allowance for U.S. Appl. No. 12/606,957, filed Oct. 27, 2009, dated Jul. 27, 2015, 19 pgs.
Hyland, Gregory E.; Supplemental Notice of Allowability for U.S. Appl. No. 12/606,957, filed Oct. 13, 2015, dated Oct. 13, 2015, 4 pgs.
Hyland, Gregory E.; U.S. Continuation Application entitled: Infrastructure Monitoring System and Method having U.S. Appl. No. 14/928,725, filed Oct. 30, 2015, 28 pgs.
Gregory E.; Final Office Action for U.S. Appl. No. 12/784,300, filed May 20, 2010, dated Feb. 11, 2014; 44 pgs.
Gregory E.; Final Office Action for U.S. Appl. No. 12/784,300, filed May 20, 2010, dated May 29, 2013, 71 pgs.
Gregory E.; Issue Notification for U.S. Appl. No. 12/784,300, filed May 20, 2010, dated Aug. 13, 2014. 1 pg.
Hyland, Gregory E.; Non-Final Office Action for U.S. Appl. No. 12/784,300, filed May 20, 2010, dated Sep. 10, 2012, 35 pgs.
Gregory E.; Non-Final Office Action for U.S. Appl. No. 12/784,300, filed May 20, 2010, dated Sep. 24, 2013; 37 pgs.
Hyland, Gregory E.; Notice of Allowance for U.S. Appl. No. 12/784,300, filed May 20, 2010, dated Apr. 23, 2014, 20 pgs.
Hyland, Gregory E.; Supplemental Notice of Allowability for U.S. Appl. No. 12/784,300, filed May 20, 2010, dated Aug. 1, 2014, 4 pgs.
Hyland, Gregory E.; Final Office Action for U.S. Appl. No. 14/450,452, filed Aug. 4, 2014, dated Aug. 23, 2016, 41 pgs.
Hyland, Gregory E.; Non-Final Office Action for U.S. Appl. No. 14/450,452, filed Aug. 4, 2014, dated Feb. 17, 2016, 98 pgs.
Keyghobad, Seyamak; Issue Notification for U.S. Appl. No. 10/298,300, filed Nov. 18, 2002, dated Oct. 8, 2008; 1 pg.
Keyghobad, Seyamak; Requirement for Restriction/ Election for U.S. Appl. No. 10/298,300, filed Nov. 18, 2002; dated Feb. 9, 2006; 11 pages.
Keyghobad, Seyamak; Issue Notification for U.S. Appl. No. 12/243,452, filed Oct. 1, 2008 dated Jun. 16, 2010; 1 pg.

(56) References Cited

OTHER PUBLICATIONS

Keyghobad, Seyamak; Issue Notification for U.S. Appl. No. 12/490,867, filed Jun. 24, 2009, dated Feb. 29, 2012; 1 pg.
Keyghobad, Seyamak; Non Final Rejection for U.S. Appl. No. 12/490,867, filed Jun. 24, 2009, dated Mar. 21, 2011; 10 pgs.
Keyghobad, Seyamak; Non Final Rejection for U.S. Appl. No. 12/490,867, filed Jun. 24, 2009, dated Oct. 4, 2010; 14 pgs.
Keyghobad, Seyamak; Notice of Allowance for U.S. Appl. No. 12/490,867, filed Jun. 24, 2006, dated Sep. 7, 2011; 6 pgs.
Keyghobad, Seyamak; Notice of Allowance for U.S. Appl. No. 12/490,867, filed Jun. 24, 2009, dated Nov. 2, 2011; 17 pgs.
Keyghobad, Seyamak; Issue Notification for U.S. Appl. No. 12/490,925, filed Jun. 24, 2009; dated Aug. 18, 2010; 1 pg.
Keyghobad, Seyamak; Non-final office action for U.S. Appl. No. 12/490,925, filed Jun. 24, 2009; dated Dec. 23, 2009; 17 pgs.
Keyghobad, Seyamak; Notice of Allowance for U.S. Appl. No. 12/490,925, filed Jun. 24, 2009, dated Aug. 2, 2010, 8 pgs.
Keyghobad, Seyamak; Issue Notification for U.S. Appl. No. 12/490,957, filed Jun. 24, 2009; dated Aug. 4, 2010; 1 pg.
Keyghobad, Seyamak; Non-final Office Action for U.S. Appl. No. 13/372,408, filed Feb. 23, 2012; dated May 25, 2012; 17 pgs.
Keyghobad, Seyamak; Notice of Allowance for U.S. Appl. No. 13/372,408, filed Feb. 13, 2012, dated Jul. 27, 2012; 11 pgs.
Keyghobad, Seyamak; Notice of Allowance for U.S. Appl. No. 13/372,408, filed Feb. 13, 2012; dated Nov. 1, 2012; 18 pgs.
Keyghobad, Seyamak; Supplemental Notice of Allowance for U.S. Appl. No. 13/372,408, filed Feb. 13, 2012; dated Aug. 2, 2012; 7 pgs.
Keyghobad, Seyamak, Issue Notification for U.S. Appl. No. 13/590,954, filed Aug. 21, 2012, dated Sep. 11, 2013, 1 pg.
Keyghobad, Seyamak; Issue Notification for U.S. Appl. No. 13/372,408, filed Feb. 13, 2012, dated Mar. 6, 2013, 1 pg.
Keyghobad, Seyamak; Non-Final Office Action for U.S. Appl. No. 13/590,954, filed Aug. 21, 2012, dated Dec. 13, 2012; 39 pgs.
Keyghobad, Seyamak; Notice of Allowance for U.S. Appl. No. 13/590,954, filed Aug. 21, 2012, dated Mar. 21, 2013, 22 pgs.
Keyghobad, Seyamak; Notice of Allowance for U.S. Appl. No. 13/590,954, filed Aug. 21, 2012, dated Jul. 9, 2013, 21 pgs.
Hyland; International Preliminary Report on Patentability for serial No. PCT/US2009/062247, filed Oct. 27, 2009, dated May 3, 2011, 7 pgs.
Hyland; International Search Report for serial No. PCT/US2009/062247, filed on Oct. 27, 2009, dated Dec. 18, 2009, 2 pgs.
Hyland, Gregory E.; Canadian Office Action for serial No. 2,741,843, filed Oct. 27, 2009, dated Dec. 8, 2015, 5 pgs.
Hyland, Gregory E.; Canadian Office Action for serial No. 2,741,843, filed Oct. 27, 2009, dated Jul. 22, 2016, 5 pgs.
Hyland, Gregory; Mexico Office Action for serial No. MX/a/2011/004330, filed Apr. 25, 2011, dated Oct. 3, 2013, 6 pgs.
Hyland, Gregory; Mexico Office Action for serial No. MX/a/2011/004330, filed Apr. 25, 2011, dated Jul. 18, 2013, 6 pgs.
Hyland, Gregory;Mexico Office Action for serial No. MX/a/2011/004330, filed Apr. 25, 2011, dated Mar. 21, 2013, 7 pgs.
Hyland; European Examination Report for serial No. EP09824079.9, filed Oct. 27, 2009, dated Nov. 13, 2015; 6 pgs.
Hyland, Gregory E.; Final Office Action for Continuation U.S. Appl. No. 14/928,725, filed Oct. 30, 2015, dated Jul. 18, 2017, 51 pgs.
Hyland, Gregory E.; Notice of Allowability for U.S. Appl. No. 14/450,452, filed Aug. 4, 2014, dated Jul. 18, 2017, 6 pgs.
Hyland, Gregory E.; Office Action for Canadian patent application No. 2,772,545, filed May 20, 2010, dated Jun. 22, 2017, 3 pgs.
Clark, Kenneth A.; Applicant-Initiated Interview Summary for U.S. Appl. No. 14/209,257, filed Mar. 13, 2014, dated Jul. 19, 2017, 7 pgs.
Clark, Kenneth A.; Office Action for Mexico Application No. MX/a/2015/011793, filed Mar. 13, 2014, dated Feb. 20, 2017, 7 pgs.
Hyland, Gregory E.; European Search Report for serial No. EP2433440, filed Nov. 18, 2011, dated Apr. 10, 2017, 6 pgs.
Hyland, Gregory E.; Notice of Allowance for U.S. Appl. No. 14/450,452, filed Aug. 4, 2014, dated Jun. 15, 2017, 17 pgs.
Hyland, Gregory E.; Canadian Office Action for Serial No. 2,741,843, filed Oct. 27, 2009, dated Apr. 25, 2017, 7 pgs.
Clark, Kenneth A.; Final Office Action for U.S. Appl. No. 14/209,257, filed Mar. 13, 2014, dated Jun. 28, 2017, 41 pgs.
Clark, Kenneth A.; Office Action for Mexico Application No. MX/a/2015/011793, filed Mar. 13, 2014, dated Jun. 20, 2017, 8 pgs.
Clark, Kenneth A.; Office Action for Australian Application No. 2014235054, filed Mar. 13, 2014, dated Jun. 2, 2017, 3 pgs.
Hyland, Gregory E.; Office Action for Canadian application No. 2,772,545, filed May 10, 2010, dated Jul. 27, 2016, 4 pgs.
Clark, Kenneth A.; Restriction Requirement for U.S. Appl. No. 14/209,257, filed Mar. 13, 2014, dated Oct. 4, 2016, 7 pgs.
Gifford, Paul; International Search Report and Written Opinion for PCT Application No. PCT/US16/36007, filed Jun. 6, 2016, dated Oct. 6, 2016, 12 pgs.
Article entitled: "Datamatic, Badger Connect for AMR Solutions", http://www.datamatic.com/badger_partnership.html; accessed on Jul. 27, 2012, 1 pg.
Hyland, Gregory E.; Australian Examination Report for serial No. 2014259545, filed Oct. 27, 2009, dated Jun. 10, 2015; 2 pgs.
Hyland; International Search Report and Written Opinion for serial No. PCT/US2010/035666, filed May 20, 2010, dated Jul. 16, 2010, 7 pgs.
Hyland; International Preliminary Report on Patentability for serial No. PCT/US2010/035666, filed May 20, 2010, dated Nov. 22, 2011, 6 pgs.
Hyland, Gregory E.; Mexico Office Action for serial No. MX/A/2011/012383, filed May 20, 2010, dated Oct. 8, 2012, 3 pgs.
Hyland, Gregory E.; Mexico Office Action for serial No. MX/A/2011/012383, filed May 20, 2010, dated May 9, 2013, 8 pgs.
Hyland, Gregory E.; Mexico Office Action for serial No. MX/A/2011/012383, filed May 20, 2010, dated Sep. 3, 2013, 10 pgs.
Hyland, Gregory E.; Mexico Final Office Action for serial No. MX/A/2011/012383, filed May 20, 2010, dated Jan. 9, 2014, 9 pgs.
European Search Report for serial No. EP2433440, filed Nov. 18, 2011, dated Nov. 28, 2012, 6 pgs.
Hyland, Gregory E.; Australian Patent Examination report for serial No. 2010249499, filed Nov. 17, 2011, dated Jun. 16, 2014, 5 pgs.
Hyland, Gregory E.; Australian Patent Examination report for serial No. 2010249499, filed Nov. 17, 2011, dated Nov. 21, 2014, 5 pgs.
Hyland, Gregory; Japanese Office Action for serial No. 2012-512048, filed May 20, 2010, dated Oct. 22, 2013, 51 pgs.
Hyland, Gregory; Decision of Rejection for Japanese serial No. 2012-512048, filed May 20, 2010, dated Apr. 22, 2014, 10 pgs.
Hyland, Gregory; Mexico Office Action for serial No. MX/a/2012/015236, filed Dec. 19, 2012, dated Jun. 13, 2013, 4 pgs.
Hyland, Gregory; Mexico Office Action for serial No. MX/a/2012/015236, filed Dec. 19, 2012, dated Oct. 3, 2013, 8 pgs.
Hyland, Gregory; Mexico Office Action for serial No. MX/a/2012/015236, filed Dec. 19, 2012, dated Dec. 3, 2013, received by foreign associate on Jan. 9, 2014, 4 pgs.
Hyland, Gregory E.; Australian Patent Examination report for serial No. 2015202223, filed May 20, 2010, dated Nov. 4, 2015, 4 pgs.
Hyland; U.S. Provisional Patent Application entitled: Water Supply Infrastructure Monitoring System and Method, having U.S. Appl. No. 61/108,770, filed Oct. 27, 2008, 11 pgs.
Hyland; U.S. Provisional Patent Application entitled: Water Supply Infrastructure Monitoring System and Method, having U.S. Appl. No. 61/180,600, filed May 22, 2009, 14 pgs.
Clark, Kenneth A.; U.S. Patent Application entitled: Systems for Measuring Priorities of Water in a Water Distribution System, U.S. Appl. No. 14/209,257, filed Mar. 13, 2014; 60 pgs.
Clark, Kenneth A.; U.S. Provisional Patent Application entitled: Systems for Measuring Properties of Water in a Water Distribution System , U.S. Appl. No. 61/794,616, filed Mar. 15, 2013; 49 pgs.
Clark, Kenneth A.; International Search Report and Written Opinion for serial No. PCT/US2014/025617, filed Mar. 13, 2014, dated Aug. 27, 2014, 48 pgs.
Huang, et al.; "The Mahalanobis-Taguchi system—Neural network algorithm for data mining in dynamic environments", Extern Systems with Appklications (online), 2009 [retrieved on Aug. 13, 2014], vol. 36, pp. 5475-5480.

(56) References Cited

OTHER PUBLICATIONS

Clark, Kenneth A.; International Preliminary Report on Patentability for PCT/US2014/025617, filed Mar. 13, 2014, dated Sep. 24, 2015, 12 pgs.
Clark, Kenneth A.; Extended European Search Report for serial No. 14771115.4, filed Mar. 13, 2014, dated Sep. 14, 2016, 8 pgs.
Stoianov, et al.; Article entitled: "Sensor Networks for Monitoring Water Supply and Sewer Systems: Lessons from Boston", Water Distribution Systems Analysis Symposium 2006; , Aug. 27-30, 2006, 17 pgs.
Perelman, et al.; Article entitled: "Event Detection in Water Distribution Systems from Multivariate Water Quality Time Series", Environmental Science & Technology, vol. 46, No. 15, Aug. 7, 2012, 8 pgs.
Palau, et al.; Article entitled: "Using Multivariate Principal Component Analysis of Injected Water Flows to Detect Anomalous Behaviors in a Water Supply System. A case Study.", Water Science and Technology: Water Supply, vol. 4, No. 3, Jun. 30, 2004, 12 pgs.
Hyland, Gregory E.; Notice of Allowance for U.S. Appl. No. 14/928,725, filed Oct. 30, 2015, dated Nov. 30, 2017, 22 pgs.
Hyland, Gregory E.; Supplemental Notice of Allowance for U.S. Appl. No. 14/928,725, filed Oct. 30, 2015, dated Dec. 28, 2017, 6 pgs.
Hyland, Gregory; Corrected Notice of Allowability for U.S. Appl. No. 14/450,452, filed Aug. 4, 2014, dated Sep. 26, 2017, 4 pgs.
Hyland, Gregory; Issue Notification for U.S. Appl. No. 14/450,452, filed Aug. 4, 2014, dated Oct. 4, 2017, 1 pg.
Clark, Kenneth A.; Non-Final Office Action for U.S. Appl. No. 14/209,257, filed Mar. 13, 2014, dated Oct. 16, 2017, 33 pgs.
Clark, Kenneth A.; Non-Final Office Action for U.S. Appl. No. 15/347,849, filed Nov. 10, 2016, dated Nov. 3, 2017, 84 pgs.
Gifford, Paul;International Preliminary Report on Patentability for PCT Application No. PCT/US16/36007, filed Jun. 6, 2016, dated Dec. 14, 2017, 9 pgs.
Vonroll Hydro—Hydrojournal, pp. 1-16 and translation, May 2008, 20 pgs.
Hyland, Gregory E.; Issue Notification for U.S. Appl. No. 14/928,725, filed Oct. 30, 2015, dated Mar. 14, 2018, 1 pg.
Hyland, Gregory E.; Supplemental Notice of Allowance for U.S. Appl. No. 14/928,725, filed Oct. 30, 2015, dated Feb. 27, 2018, 6 pgs.
Clark, Kenneth A.; Final Office Action for U.S. Appl. No. 15/347,849, filed Nov. 10, 2016, dated Jun. 1, 2018, 29 pgs.
Wikipedia; Article entitled: "Water turbine", located at (https://en.wikipedia.org/wiki/Water_turbine), 11 pgs.
Clark, Kenneth A.; Notice of Allowance for U.S. Appl. No. 14/209,257, filed Mar. 13, 2014, dated Jun. 27, 2018, 26 pgs.
Clark, Kenneth A.; Examination Report for Australian application No. 2018200410, filed Mar. 13, 2014, dated Jun. 28, 2018, 4 pgs.
Hyland, Gregory E.; Non-Final Office Action for U.S. Appl. No. 15/895,062, filed Feb. 13, 2018, dated Oct. 25, 2018, 72 pgs.
Clark, Kenneth A.; Issue Notification for U.S. Appl. No. 14/209,257, filed Mar. 13, 2014, dated Sep. 26, 2018, 1 pg.
Clark, Kenneth A.; Notice of Allowance for U.S. Appl. No. 15/347,849, filed Nov. 10, 2016, dated Sep. 18, 2018, 20 pgs.
Hyland, Gregory E.; Extended European Search Report for serial No. 18214263.8, filed Oct. 27, 2009, dated Sep. 2, 2019, 11 pgs.
Clark, Kenneth A.; Non-Final Office Action for U.S. Appl. No. 16/118,914, filed Aug. 31, 2018, dated Sep. 9, 2019, 107 pgs.
Whittle, et al.; Article entitled: "WaterWise©SG: A Testbed for Continuous Monitoring of the Water Distribution System in Singapore", Water Distribution Analysis 2010—WDSA2010, Tucson, AZ, USA, Sep. 12-15, 2010; 16 pgs.
Clark, Kenneth A.; Examination Report for Australian patent application No. 2018253559, filed Mar. 13, 2014, dated Jul. 8, 2019, 3 pgs.
Gifford, Paul S.; European Search Report for serial No. 16804634.0, filed Jun. 6, 2016, dated Jul. 25, 2019, 21 pgs.
Shafiee, et al.; Article entitled: "Integrating Evolutionary Computation and Sociotechnical Simulation for Flushing Contaminated Water Distribution Systems", Genetic and Evolutionary Computation, ACM, Jul. 1, 2012, pp. 315-322 (8 pgs).
Hyland, Gregory E.; Corrected Notice of Allowance for U.S. Appl. No. 15/895,062, filed Feb. 13, 2018, dated Mar. 6, 2019, 7 pgs.
Hyland, Gregory E.; Issue Notification for U.S. Appl. No. 15/895,062, filed Feb. 13, 2018, dated Mar. 27, 2019, 1 pg.
Gifford, Paul S.; European Search Report for serial No. 16804634.0, filed Jun. 6, 2016, dated Mar. 11, 2019, 19 pgs.
Whittle, et al; Article entitled: "WaterWise@SG: A Testbed for Continuous Monitoring of the Water Distribution System in Singapore", Water Distribution Analysis 2010, Dec. 21, 2011, 16, pgs.
Hyland, Gregory E.; Notice of Allowance for U.S. Appl. No. 15/895,062, filed Feb. 13, 2018, dated Dec. 26, 2018, 11 pgs.
Hyland, Gregory E.; Office Action for Canadian patent application No. 2,997,878, filed Oct. 27, 2009, dated Dec. 10, 2018, 4 pgs.
Icelandic Building Research Institute, et al.; "Monitoring corrosion in district heating systems", Nordic Innovation, Project No. 00071, Final Report, pp. 1-254, May 2004 (May 2004).
Hyland, Gregory E.; Extended European Search Report for serial No. 18184468.9, filed May 20, 2010, dated Dec. 3, 2018, 9 pgs.
Hyland, Gregory E.; Extended European Search Report for serial No. 18184481.2, filed May 20, 2010, dated Dec. 3, 2018, 9 pgs.
Clark, Kenneth A.; Issue Notification for U.S. Appl. No. 14/209,257, filed Mar. 13, 2014, dated Dec. 22, 2018, 1 pg.
Clark, Kenneth A.; Issue Notification for U.S. Appl. No. 15/347,849, filed Nov. 10, 2016, dated Jan. 23, 2019, 1 pg.
Hyland, Gregory E.; Office Action for Canadian patent application No. 2,997,878, filed Oct. 27, 2009, dated Sep. 27, 2019, 5 pgs.
Clark, Kenneth A.; Non-Final Office Action for U.S. Appl. No. 16/118,907, filed Aug. 31, 2018, dated Oct. 11, 2019, 104 pgs.
Clark, Kenneth A.; Non-Final Office Action for U.S. Appl. No. 16/118,664, filed Aug. 31, 2018, dated Oct. 1, 2019, 95 pgs.
dictionary.com; definition of "turbine", accessed on Sep. 3, 2019, 1 pg.
Hyland, Gregory E.; Office Action for Canadian patent application No. 2,997,878, filed Oct. 27, 2009, dated Apr. 2, 2020 7 pgs.
Clark, Kenneth A.; Final Office action for U.S. Appl. No. 16/118,907, filed Aug. 31, 2018, dated Apr. 16, 2020, 35 pgs.
Clark, Kenneth A.; Final Office Action for U.S. Appl. No. 16/118,664, filed Aug. 31, 2018, dated Apr. 7, 2020, 23 pgs.
Clark, Kenneth A.; Office Action for Canadian application No. 2,900,965, filed Mar. 13, 2014, dated Jun. 12, 2020, 4 pgs.
Clark, Kenneth A.; Examination Report for Australian patent application No. 2018253559, filed Mar. 13, 2014, dated Apr. 28, 2020, 3 pgs.
Gifford, Paul S.; Office Action for Canadian patent application No. 2,987,661, filed Jun. 6, 2016, dated Apr. 21, 2020, 3 pgs.
Clark, Kenneth A.; Final Office Action for U.S. Appl. No. 16/118,914, filed Aug. 31, 2018, dated Mar. 23, 2020, 52 pgs.
Clark, Kenneth A.; Examination Report for Australian patent application No. 2018253559, filed Mar. 13, 2014, dated Jan. 17, 2020, 3 pgs.
Clark, Kenneth A.; Applicant-Initiated Interview Summary for U.S. Appl. No. 16/118,664, filed Mar. 31, 2018, dated Dec. 26, 2019, 6 pgs.
Gifford, Paul S.; Office Action for Canadian patent application No. 2,987,661, filed Jun. 6, 2016, dated Nov. 26, 2019, 4 pgs.
Gifford, Paul S.; Office Action for Canadian patent application No. 2,987,661, filed Jun. 6, 2016, dated Aug. 17, 2020, 3 pgs.
Hyland, Gregory E.; Office Action for Canadian patent application No. 2,997,878, filed Oct. 27, 2009, dated Nov. 25, 2020, 7 pgs.
Clark, Kenneth A.; Office Action for Canadian application No. 2,900,965, filed Mar. 13, 2014, dated Oct. 27, 2020, 4 pgs.
Hyland, Gregory E.; Office Action for Canadian patent application No. 2,997,878, filed Oct. 27, 2009, dated Jul. 16, 2020, 7 pgs.
Hunaidi, et al., "A new System for locating leaks in urban water distribution pipes", International Journal of Management of Environmental Quality, Jan. 31, 2006, pp. 450-466, Retrieved from the internet: <http://web.mit.edu/parmstr/Public/NRCan/nrcc48357.pdf>, 19 pgs.
Hyland, Gregory E.; Office Action for European serial No. 18214263.8, filed Oct. 27, 2009, dated Jul. 14, 2020, 5 pgs.

(56) References Cited

OTHER PUBLICATIONS

Clark, Kenneth A.; Office Action for European serial No. 14771115.4, filed Mar. 13, 2014, dated Sep. 9, 2020, 4 pgs.
Clark, Kenneth A.; Non-Final Office Action for U.S. Appl. No. 16/118,914, filed Aug. 31, 2018, dated Mar. 4, 2021, 55 pages.
Hyland, Gregory E.; Office Action for European application No. 18214263.8, filed Oct. 27, 2009, dated Mar. 1, 2021, 7 pgs.
Clark, Kenneth A.; Requirement for Restriction/Election for U.S. Appl. No. 16/118,664, filed Aug. 31, 2018, dated Apr. 27, 2021, 29 pgs.

* cited by examiner

1100

| Description | Turbidity | Temperature | Pressure | pH | Chlorine |
|---|---|---|---|---|---|
| device 0 | | | 100.2 psi | | |
| device 1 | | | 1.3 psi | | |
| device 2 | | | 75.2 psi | | |
| device 3 | | | 78.2 psi | | |
| device 4 | | | 80.2 psi | | |
| device 5 | | | 78.2 psi | | |
| device 6 | | | 71.2 psi | | |
| V2 device | 22.3 ntu | 18.3 F | 19.2 psi | 83.2 pH | 4.0 ppm |

DISTRIBUTION SYSTEM MONITORING

REFERENCE TO RELATED APPLICATION

This application claims the benefit of U.S. Provisional Application No. 62/171,897, filed Jun. 5, 2015, which is hereby specifically incorporated by reference herein in its entirety.

BACKGROUND

A utility provider may install and maintain infrastructure to provide utility services to its customers. For example, a water utility provider may implement a fluid distribution system to distribute water to its customers. The fluid distribution system may be maintained, such as to maintain the integrity of the fluid distribution system and the quality of the fluid (e.g., water) within the fluid distribution system.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

Figure 13C:
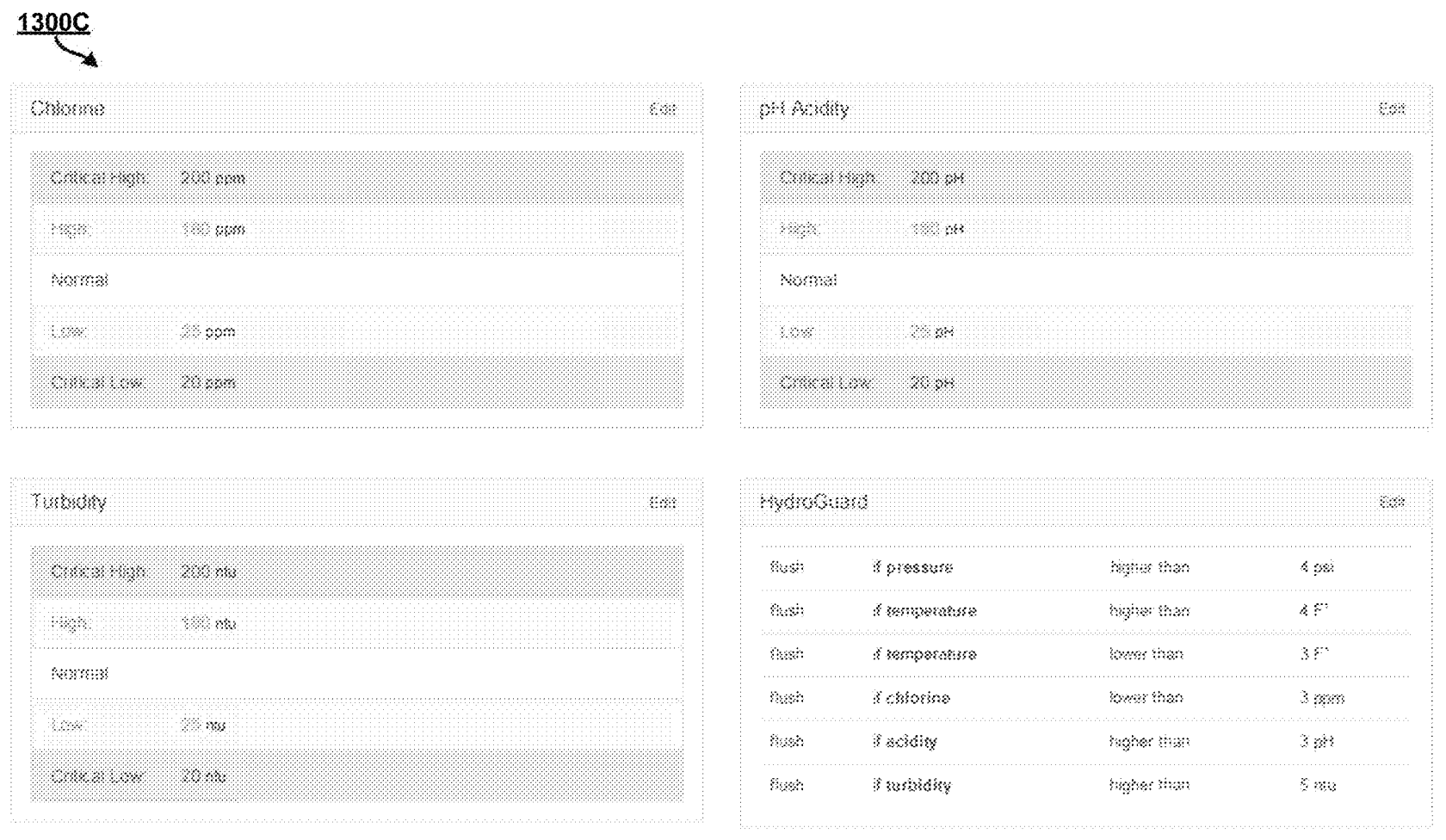
Figure 13D:
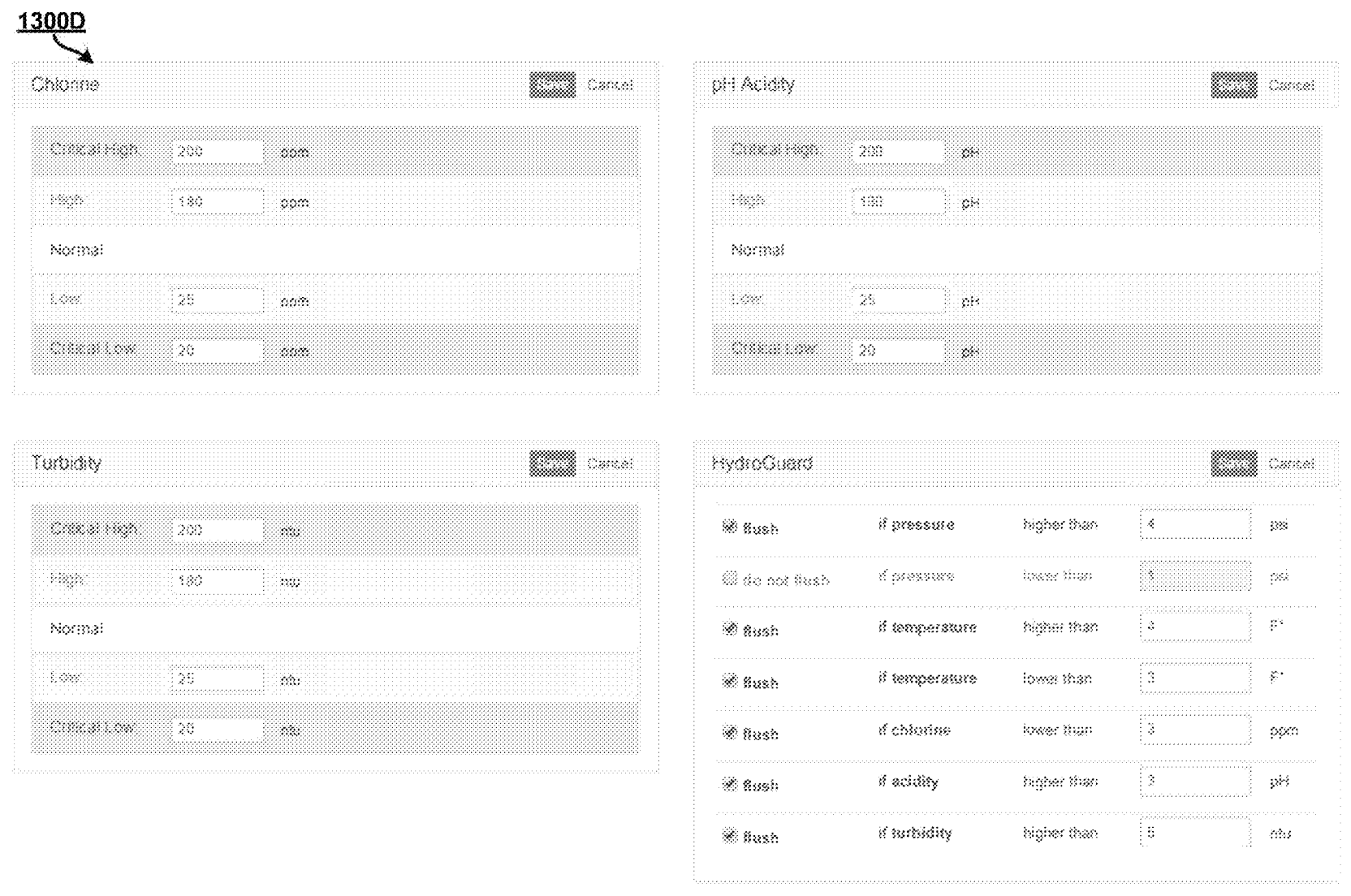

FIGS. 9-15C represent screenshots 900-1500C of a system for configuring and managing a monitoring device according to examples of the present disclosure.

DETAILED DESCRIPTION

Figure 1:
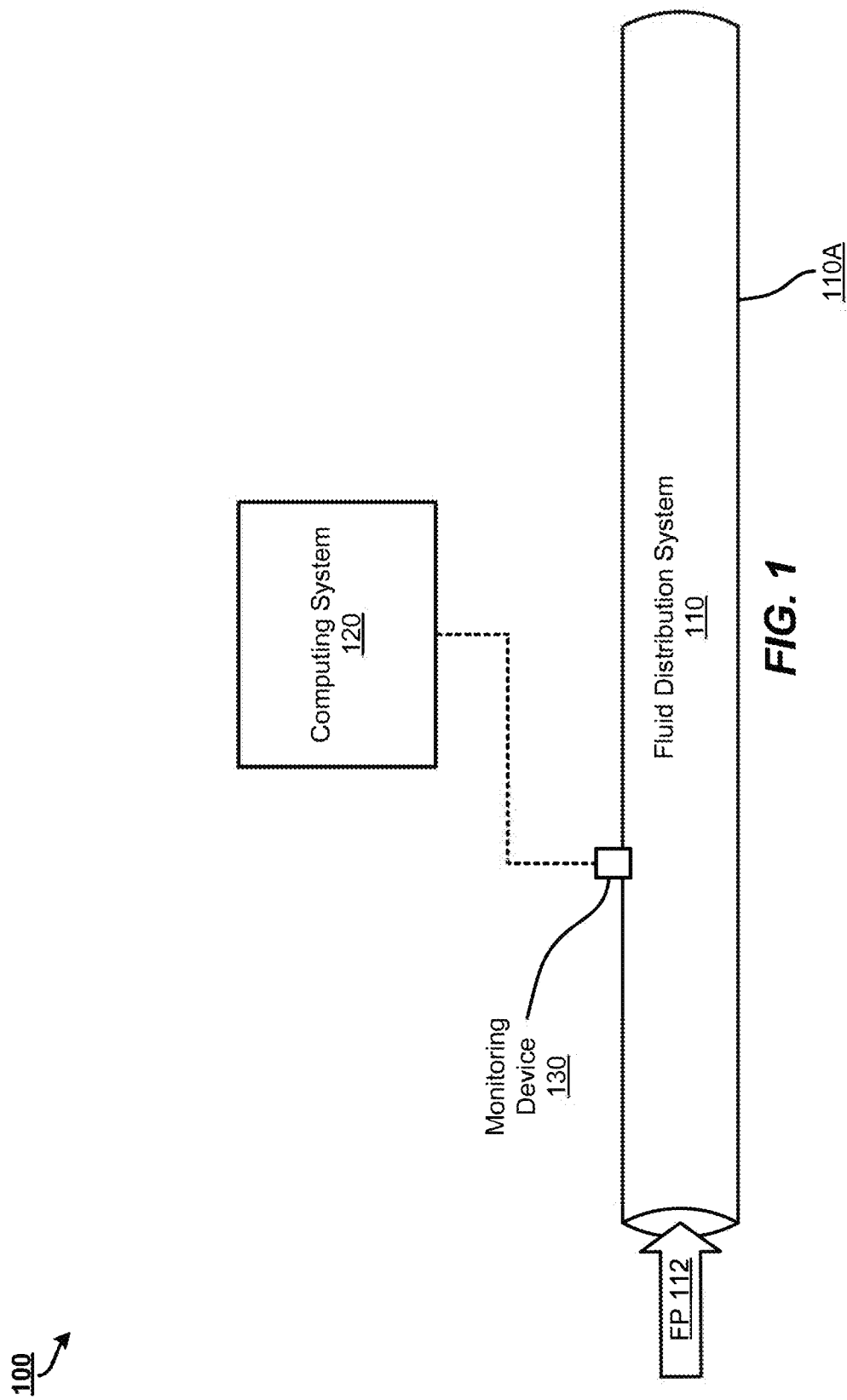
FIG. 1 illustrates a diagram of an environment to monitor a fluid distribution system according to examples of the present disclosure.

A utility provider may utilize a fluid distribution system to distribute fluids such as water or gas to its customers. To provide the fluid to its customers effectively, the utility provider may monitor the efficiency and integrity of the fluid distribution system. For example, the utility provider may monitor pressure, temperature, turbidity, pH, and chlorine, among other parameters, within the fluid distribution system.

Various implementations are described herein by referring to several examples of monitoring a fluid distribution system. The fluid monitoring system may monitor multiple aspects of the performance of a fluid distribution system and the quality of the fluid within the fluid distribution system, including at least pressure, pH, turbidity, temperature, chlorine, etc. It should be understood that, although the present disclosure discusses a multi-parameter fluid monitoring system, the fluid monitoring system may utilize a single parameter as well as multiple parameters.

In one example implementation according to aspects of the present disclosure, a method comprises receiving, at a monitoring device, fluid parameter information from a sensor in a fluid distribution system. The method further comprises collecting, by the monitoring device, sampling data of the fluid parameter information from the sensor based on predetermined criteria. The method further comprises receiving, by the monitoring device, a request to collect transient data from the sensor. The method further comprises collecting, by the monitoring device, transient data of the fluid parameter information from the sensor based on predetermined criteria. The method further comprises communicating the sampling data and the transient data to another device.

In another example implementation according to aspects of the present disclosure, an apparatus may comprise a monitoring device and a sensor array connected to the monitoring device. The monitoring device may comprise a power source, an antenna, and a parameter sensing portion configured to monitor a parameter of a fluid distribution system.

In another example implementation according to aspects of the present disclosure, a monitoring device may comprise a power source, an antenna, and a parameter sensing portion configured to monitor a pressure parameter, a temperature parameter, a turbidity parameter, a pH parameter, and a chlorine parameter of a fluid distribution system. The monitoring device may be configured to connect to a sensor array. The sensor array may comprise a pressure sensor, a temperature sensor, a turbidity sensor, a pH sensor, and a chlorine sensor.

In another example implementation according to aspects of the present disclosure, a system for sensing parameters in a fluid distribution system. The system may comprise a monitoring device, a sensor array connected to the monitoring device, and a computing system. The monitoring device may comprise a parameter sensing module configured to monitor a parameter of the fluid distribution system, a power source, and an antenna. The computing system may comprise a processing resource and a computer-readable storage medium. The computing system may be configured to receive configuration data defining a configuration profile for the monitoring device. The configuration profile may be relating to a parameter configuration of the monitoring device. The computing system may be further configured to communicate the configuration data to the monitoring device.

Other examples are described in the present disclosure. It should be understood that the features of the disclosed examples may be combined in various combinations. It should also be understood that certain features may be omitted while other features may be added.

The present disclosure enables monitoring a fluid distribution system. For example, a fluid distribution system may be monitored based on parameters such as pressure, temperature, turbidity, pH, and/or chlorine, among others. In examples, multiple parameters may be monitored by the same monitoring device, although a monitoring device may also monitor a single parameter in examples. These and other advantages will be apparent from the description that follows.

Figure 2:
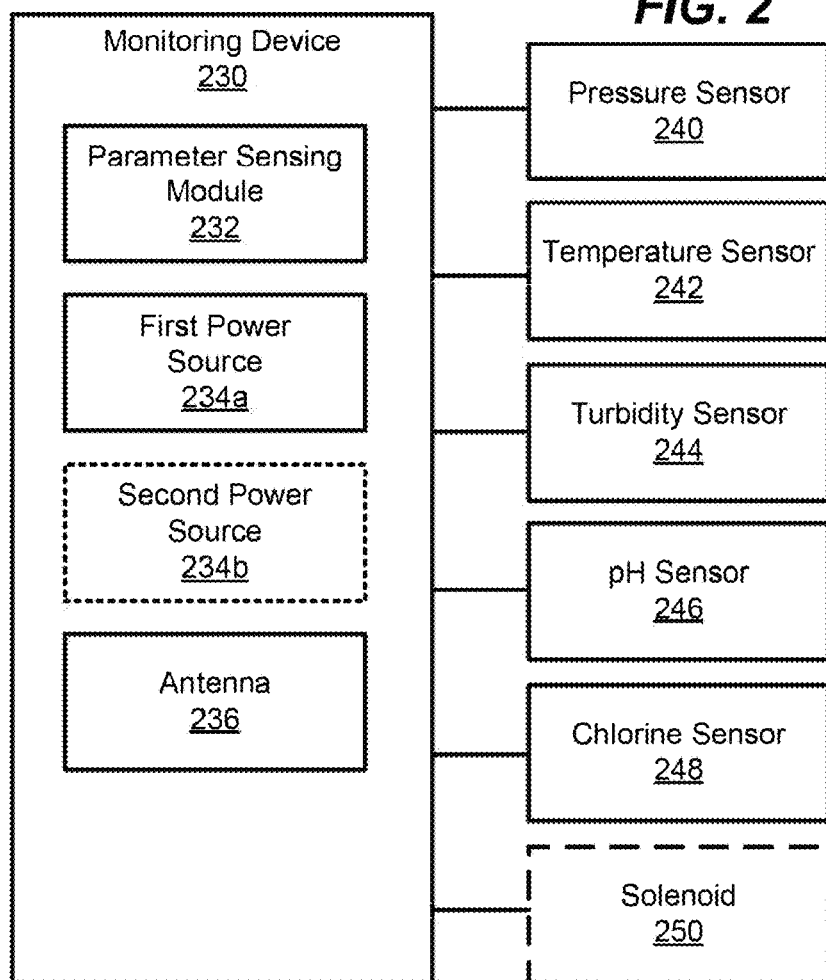
FIG. 2 illustrates a block diagram of a monitoring device to monitor a fluid distribution system, such as fluid distribution system of FIG. 1, according to examples of the present disclosure.
Figure 3:
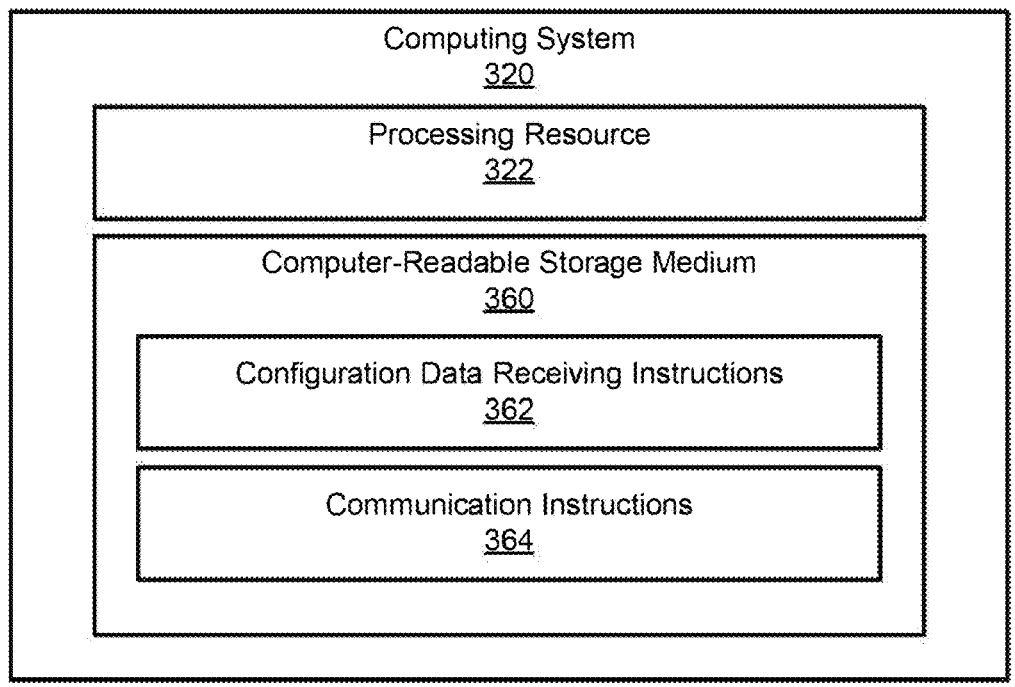
FIG. 3 illustrates a computer-readable storage medium storing instructions to monitor a fluid distribution system according to examples of the present disclosure.

FIGS. 1-3 comprise particular components, modules, instructions, engines, etc. according to various examples as described herein. In different implementations, more, fewer, and/or other components, modules, instructions, engines, arrangements of components/modules/instructions/engines, etc. may be used according to the teachings described herein. In addition, various components, modules, engines, etc. described herein may be implemented as instructions stored on a computer-readable storage medium, hardware modules, special-purpose hardware (e.g., application specific hardware, application specific integrated circuits (ASICs), embedded controllers, hardwired circuitry, etc.), or some combination or combinations of these.

Generally, FIGS. 1-3 relate to components, modules, and instructions of a computing system. It should be understood that the computing system may comprise any appropriate type of computing system and/or computing device, including for example smartphones, tablets, desktops, laptops, workstations, servers, smart monitors, smart televisions, digital signage, scientific instruments, retail point of sale devices, video walls, imaging devices, peripherals, networking equipment, wearable computing devices, or the like.

FIG. 1 illustrates a diagram of an environment 100 to monitor a fluid distribution system 110 according to examples of the present disclosure. In examples, monitoring device 130 monitors a parameter or parameters of a fluid distribution system 110. For example, the monitoring device 130 may monitor pressure, temperature, turbidity, pH, and/or chlorine within the fluid distribution system 110.

As illustrated, the environment 100 comprises a fluid distribution system 110, which may further comprise a pipe 110A. Although illustrated as the pipe 110A, it should be understood that the fluid distribution system 110 may be a plurality of pipes and other fluid distribution system components connected together to form the fluid distribution system 110, of which the pipe 110A is a portion.

Generally, fluid distribution system 110 may be used to distribute fluids such as water to customers of a utility provider, for example. The fluid distribution system 110 may comprise various and numerous components, such as pipes (e.g., pipe 110A), hydrants, valves, couplers, corporation stops, and the like, as well as suitable combinations thereof. In examples, the fluid distribution system 110 may be partially or wholly subterranean, or portions of the fluid distribution system 110 may be subterranean, while other portions of the fluid distribution system 110 may be non-subterranean (i.e., above ground). For example, a pipe such as pipe 110A may be partially or wholly subterranean while a hydrant or valve (not shown) connected to the pipe 110A may be partially or wholly non-subterraneous. In other examples, the pipe 110A may be partially subterraneous in that the pipe 110A has portions exposed, such as to connect testing and/or monitoring devices (e.g., monitoring device 130) to the pipe 110A.

The monitoring device 130 may utilize one or more sensors to monitor the fluid distribution system 110. For example, the monitoring device 130 may utilize a pressure sensor, a temperature sensor, a turbidity sensor, a pH sensor, and/or a chlorine senor. These sensors may be connected to a port or ports on the monitoring device. For example, as described herein, the monitoring device may comprise a port for each of the sensors.

The monitoring device may also comprise an antenna configured to enable the monitoring device to communicate with a computing system such as computing system 120. The computing system 120 may represent any of a variety of computing systems, such as a computing host of a utility provider, a collector node to collect data from the monitoring device 130, another monitoring device, or any other suitable computing system.

The monitoring device 130 may transmit the first and second acoustical signals respectively to the computing system 120 via a wired or wireless network or other communicative path illustrated in FIG. 1 as a dotted line. In examples, such as shown in FIG. 1, the monitoring device 130 and the computing system 120 may be communicatively coupleable to one another. In examples, the monitoring device 130 may comprise transceivers, which may communicate data between the monitoring device 130 and the computing system 120, which may comprise an interface (not shown) for transmitting and receiving the data. The transceivers may be any suitable device for sending, receiving, or sending and receiving data, such as a receiver, a transmitter, a transmitter-receiver, and/or a transceiver. It should be appreciated that any suitable communication technique may be implemented to transmit the data between the monitoring device 130 and the computing system 120. In examples, cellular technologies such as global system for mobile communications (GSM), general packet radio service (GPRS), code division multiple access (CDMA), short message service (SMS), or other suitable protocol may be utilized. Other techniques may also be utilized, including radio frequency, infrared, Bluetooth®, automated meter reading (AMR), automated meter infrastructure (AMI), or other wireless and/or wired communications techniques.

The dotted line of FIG. 1 illustrates communicative paths between and among the monitoring device 130 and the computing system 120. The path generally represents a network that may comprise hardware components and computers interconnected by communications channels that allow sharing of resources and information. The network may comprise one or more of a cable, wireless, fiber optic, or remote connection via a telecommunication link, an infrared link, a radio frequency link, or any other connectors or systems that provide electronic communication. The network may comprise, at least in part, an intranet, the internet, or a combination of both. The network may also comprise intermediate proxies, routers, switches, load balancers, and the like. The paths followed by the network between the devices as depicted in FIG. 1 represent the logical communication paths between the monitoring device 130 and the computing system 120, not necessarily the physical paths between and among the devices.

In examples, the monitoring device 130 may be of a three-piece construction. For example, the monitoring device 130 may comprise an antenna section, a power source section, and an electronics section.

In other examples, the monitoring device 130 may be of a four-piece construction. For example, the monitoring device 130 may comprise an antenna section, a first power source section, a second power source section, and an electronics section.

In an example, the monitoring device 130 may be enabled to monitor a fluid level within a fluid tank (not shown). A pressure sensor connected to or a part of the monitoring device 130 may be installed or otherwise inserted into a fluid tank. The monitoring device 130 may then be configured to measure the fluid level within the fluid tank by sensing the fluid level within the fluid tank. The fluid level may be returned as a tank level such as in feet, pounds per square inch (PSI), etc.

In an example, when fluid pressure is measured with a sensor, the measured pressure represents the pressure at the location it was measured. In some situations, it is advantageous to know true potential energy of the fluid. True potential energy is the measured pressure plus a known elevation of the fluid at the sensor. The elevation may be input by a customer or technician, may be based on a topology or elevation map, or may be known in some other way.

Although not shown in FIG. 1, it should be appreciated that the computing system 120 may comprise additional components. For example, the computing system 120 may comprise a processing resource 122 that represents generally any suitable type or form of processing unit or units capable of processing data or interpreting and executing instructions. The processing resource 122 may be one or more central processing units (CPUs), microprocessors, digital signal processors, and/or other hardware devices suitable for retrieval and execution of instructions. The instructions may be stored, for example, on a memory resource (not shown), such as computer-readable storage medium 360 of FIG. 3, which may comprise any electronic, magnetic, optical, or other physical storage device that store executable instructions. Thus, the memory resource may be, for example, random access memory (RAM), electrically-erasable programmable read-only memory (EEPROM), a storage drive, an optical disk, and any other suitable type of volatile or non-volatile memory that stores instructions to cause a programmable processor (i.e., processing resource) to perform the techniques described herein. In examples, the memory resource comprises a main memory, such as a RAM in which the instructions may be stored during runtime, and a secondary memory, such as a nonvolatile memory in which a copy of the instructions is stored.

Additionally, the computing system 120 may comprise engines for executing programmatic instructions. In examples, the engines may be a combination of hardware and programming. The programming may be processor executable instructions stored on a tangible memory, and the hardware may comprise processing resource, for example, for executing those instructions. Thus a memory resource (not shown) can be said to store program instructions that when executed by the processing resource implement the engines described herein. Other engines may also be utilized to comprise other features and functionality described in other examples herein.

Alternatively or additionally, the computing system 120 may comprise dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein. In some implementations, multiple processing resources (or processing resources utilizing multiple processing cores) may be used, as appropriate, along with multiple memory resources and/or types of memory resources.

Additionally, the computing system 120 may comprise a display. The display may be or comprise a monitor, a touchscreen, a projection device, and/or a touch/sensory display device. The display may display text, images, and other appropriate graphical content. The computing system 120 may also comprise a network interface to communicatively couple the computing system 120 to the monitoring device 130 via the network and to other computing systems and/or computing devices. The computing system 120 may also comprise any suitable input and/or output device, such as a mouse, keyboard, printer, external disk drive, or the like.

FIG. 2 illustrates a block diagram of a monitoring device 230 to monitor a fluid distribution system, such as fluid distribution system 110 of FIG. 1, according to examples of the present disclosure. The computing system monitoring device 230 may comprise a parameter sensing module 232, a first power source 234a, and an antenna 236. A second power source 234b is illustrated and may be comprised in some examples or omitted in other examples.

In examples, the modules described herein may be a combination of hardware and programming instructions. The programming instructions may be processor executable instructions stored on a tangible memory resource such as a computer-readable storage medium or other memory resource, and the hardware may comprise a processing resource for executing those instructions. Thus the memory resource can be said to store program instructions that when executed by the processing resource implement the modules described herein.

Other modules may also be utilized as will be discussed further below in other examples. In different implementations, more, fewer, and/or other components, modules, instructions, and arrangements thereof may be used according to the teachings described herein. In addition, various components, modules, etc. described herein may be implemented as computer-executable instructions, hardware modules, special-purpose hardware (e.g., application specific hardware, application specific integrated circuits (ASICs), and the like), or some combination or combinations of these.

Figure 7:
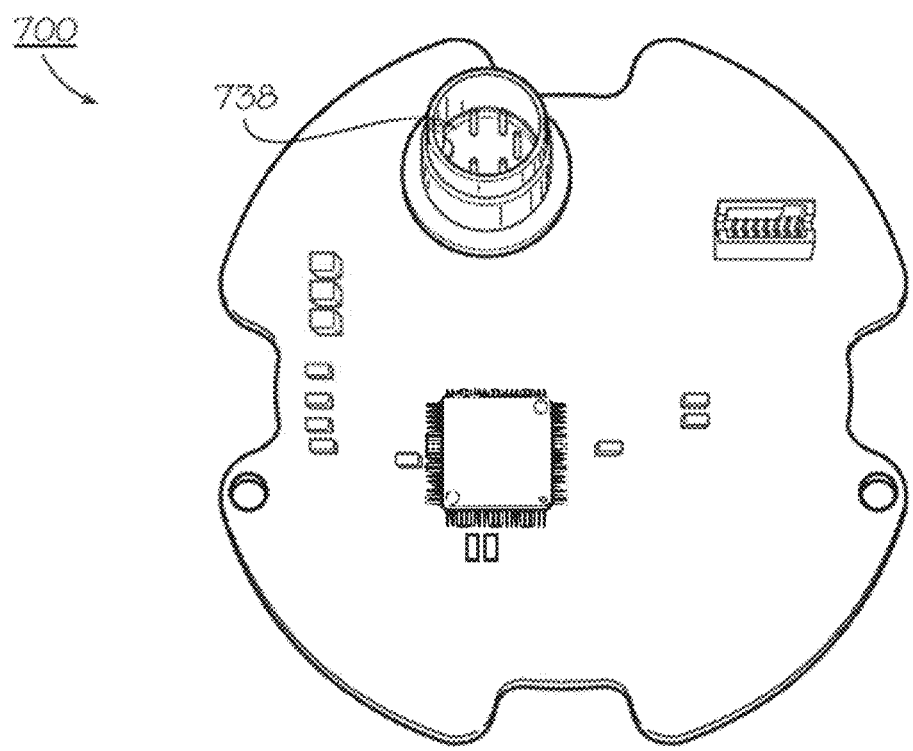
FIG. 7 illustrates a circuit board of a parameter sensing portion having one sensor port according to examples of the present disclosure.
Figure 8:
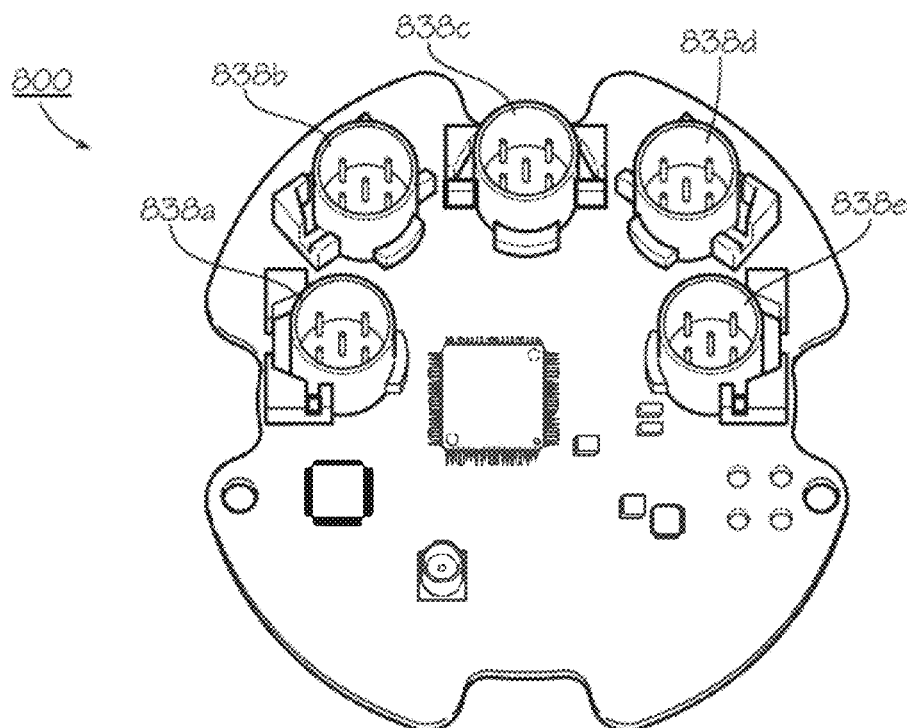
FIG. 8 illustrates another circuit board of a parameter sensing portion having five sensing ports according to examples of the present disclosure.

The parameter sensing module 232 monitors conditions of the water distribution system, including a fluid within the water distribution system, using sensors that sense various parameters of the water distribution system's fluid including pressure, temperature, turbidity, pH, and chlorine levels. The parameter sensing module 232 may be a printed circuit board (PCB) or other electrical components configured to receive electronic signals, either via wires or wirelessly, from sensors such as pressure sensor 240, temperature sensor 242, turbidity sensor 244, pH sensor 246, and/or chlorine sensor 248. Additionally, the monitoring device 230 may be connected to a solenoid 250. The parameter sensing module 232 may operate the solenoid 250 to cause a flushing operation to be performed in the fluid distribution system. Examples of parameter sensing modules as PCBs are illustrated in FIGS. 7 and 8.

As shown in those figures, the parameter sensing module 232 may comprise a sensor port or ports for connecting a sensor to the parameter sensing module 232. In examples, the sensors may communicate with the parameter sensing module 232 wirelessly, such as using near field communication (NFC), Bluetooth®, radio frequency, infrared, or other suitable wireless techniques.

In examples, the parameter sensing module 232 comprises a processing resource, such as a central processing units (CPUs), microprocessors, digital signal processors, and/or other hardware devices suitable for retrieval and execution of instructions. The parameter sensing module 232 may also comprise suitable memory such as random access memory (RAM), electrically-erasable programmable read-only memory (EPPROM), a storage drive, an optical disk, and any other suitable type of volatile or non-volatile memory that stores instructions to cause a programmable processor (i.e., the processing resource) to perform the techniques described herein. The parameter sensing module 232 may comprise additional electrical components in other examples.

The parameter sensing module 232 is configured to receive data from connected sensors indicative of the parameters sensed by the sensors. The parameter sensing module 232 may log/store the data and/or transmit the data, in whole or in part, to a host computing system such as computing system 120 of FIG. 1. The parameter sensing module 232 may also transmit event notifications when certain parameter conditions are triggered, such as if a pressure level exceeds a threshold. The trigger events may also cause the parameter sensing module 232 to operate a solenoid (e.g., solenoid 250) to cause a flushing operation to be performed in the fluid distribution system.

Each sensor may have a configurable reading period (e.g., pressure every 15 seconds, chlorine every 2 minutes, etc.). In these cases, the sensors perform the appropriate reading at the defined time, which may be preconfigured and/or user customizable. In examples, a threshold can be set, such as for pressure, and if threshold for pressure is exceeded, a flushing operation may occur. Likewise, flushing may occur when any of the parameters is sensed as exceeding a high threshold, not meeting a low threshold, falling outside of a threshold range, and/or falling within a threshold range, depending on the desired settings.

In examples, the parameter sensing module 232 may be encased in a potting material such as epoxy or other suitable material to protect the parameter sensing module 232 from adverse elements, such as water, ice, dirt, dust, and the like.

The first power source 234a may be any suitable power source that supplies electric energy to the monitoring device 230 and/or its individual component modules, directly or indirectly. In examples, the first power source 234a may be a suitable battery, such as a lithium polymer battery.

In examples, a second power source 234b may be implemented. In some examples, the second power source 234b acts as a backup battery for the first power source 234a. In additional examples, the second power source 234b provides additional power to increase the overall usable life of the monitoring device 230 and/or to power additional devices connected to the monitoring device 230, such as a solenoid valve to alter the flow of a fluid through the fluid distribution system.

In examples, the first power source 234a and/or the second power source 234b may be changed, such as by a field technician or through a refurbishing process by the manufacturer of the monitoring device 230. The first power source 234a and/or the second power source 234b may be encased in a potting material such as epoxy or other suitable material to protect the first power source 234a and/or the second power source 234b from adverse elements, such as water, ice, dirt, dust, and the like.

In examples including the second power source 234b, voltage may be decreased for certain components such as the parameter sensing module 232 or increased for higher voltage components such as an attached solenoid 250. In an example, both power sources 234a and 234b may be 3.6 volts arranged in series to operate at 7.2 volts for a solenoid while the voltage is bucked down to 3.6v to operate the parameter sensing module 232, the antenna 236, etc. In examples, solar and/or fluid generating power options are available.

The antenna 236 enables the monitoring device 230 to communicate with other devices, such as computing system 120 of FIG. 1, or any other suitable device, such as another monitoring device (not shown). The communications may be one directional (the monitoring device 230 sends information but does not receive information or the monitoring device 230 receives information but does not send information) or bi-directional (the monitoring device 230 sends and receives information).

In examples, antenna 236 is contained within an assembly that causes the antenna 236 to be aligned the same direction with respect to the rest of the monitoring device 230 when the antenna is installed. This enables more predictable communication and behavior from the antenna 236. In examples, a global positioning system (GPS) antenna (not shown) may be integrated with or otherwise comprised in antenna 236. The GPS antenna may also be configured to align the same direction when the GPS antenna is installed. The antenna 236, optionally including the GPS antenna, may be encased in a potting material such as epoxy or other suitable material to protect antenna 236 from adverse elements, such as water, ice, dirt, dust, and the like.

In some examples, during the manufacture of the antenna, a hot melt technique may be implemented. In this example, hot glue is applied by potting the hot glue to hold the antenna in place, then potting over the glue and antenna. This provides a more efficient assembly process.

In examples, the sensor may be connected to the monitoring device 230 through a jumper. When the sensor is connected to the jumper, the power circuit is "closed" thereby causing the monitoring device 230 to power on. In this way, the jumper acts as a mechanical switch and "enables by connection" the monitoring device 230. When a sensor is connected, an initialization process begins and may comprise preforming the following: 1) boots up the monitoring device 230; 2) establishes a communicative connection to a nearby receiver through the antenna 236, 3) synchronizes with GPS, 4) transmits a GPS location to a host (e.g., the computing system 120 of FIG. 1). In this way, the monitoring device 230 is a self-identifying GPS locating device. While this process may be performed automatically, it may also be performed manually.

FIG. 3 illustrates a computer-readable storage medium 360 storing instructions 362 and 364 to monitor a fluid distribution system according to examples of the present disclosure. The computer-readable storage medium 360 is non-transitory in the sense that it does not encompass a transitory signal but instead is made up of one or more memory components configured to store the instructions 362 and 364. The computer-readable storage medium 360 may be representative of a memory resource and may store machine executable instructions 362 and 364, which are executable on a computing system such as computing system 120 of FIG. 1 as well as the computing system 320 of FIG. 3 in conjunction with processing resource 322.

In the example shown in FIG. 3, the instructions 362 and 364 may comprise configuration data receiving instructions 362 and communication instructions 364. The configuration data receiving instructions 362 enabling receiving configuration data defining a configuration profile for a monitoring device (e.g., monitoring device 130 of FIG. 1 and monitoring device 230 of FIG. 2), the configuration profile relating to a parameter configuration of the monitoring device. The communication instructions 364 enable communication of the configuration data to the monitoring device.

Figure 4:
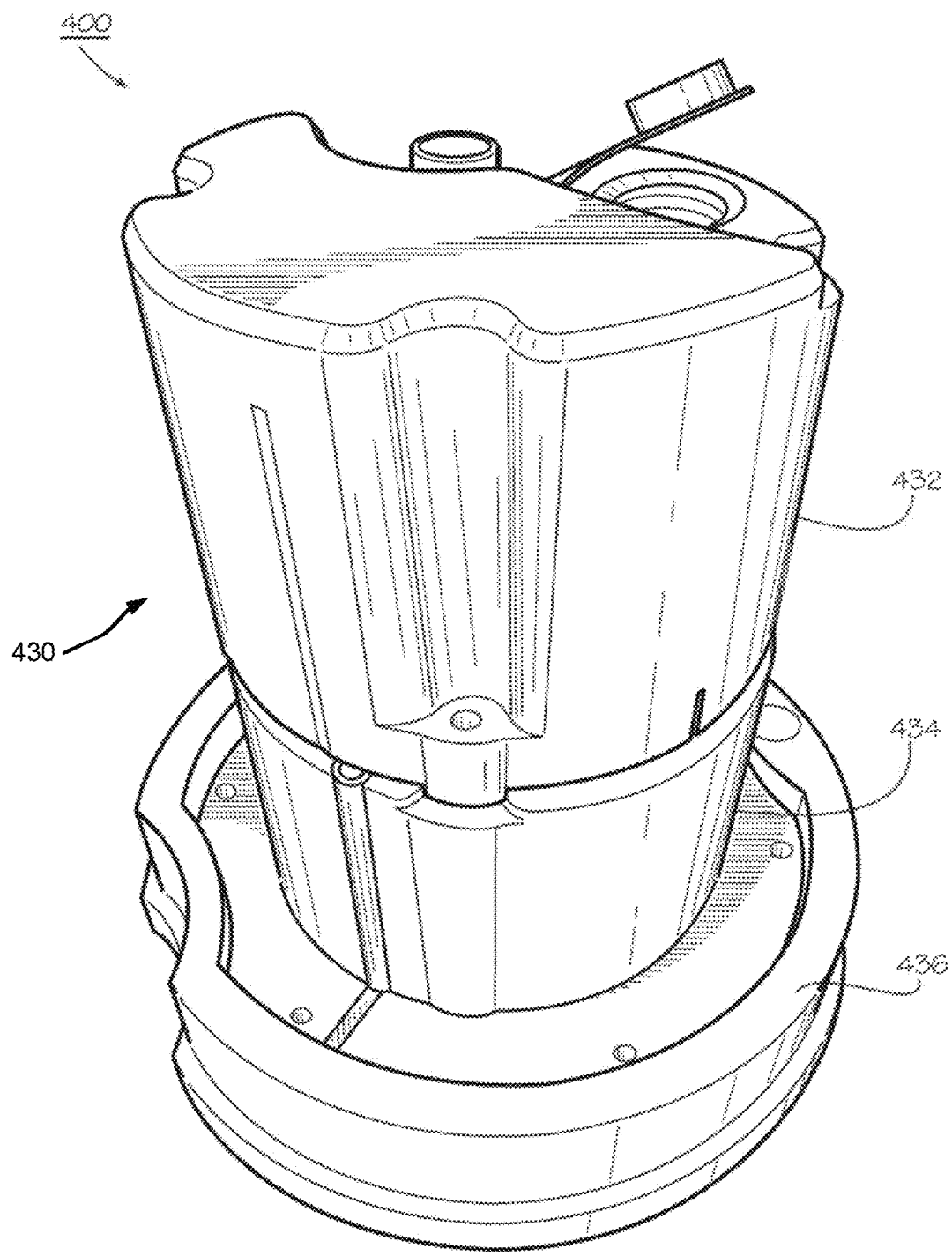
FIG. 4 illustrates an assembled view of a monitoring assembly according to examples of the present disclosure.

FIG. 4 illustrates an assembled view of a monitoring assembly 400 according to examples of the present disclosure. The monitoring device 430 may comprise a parameter sensing portion 432, a power supply portion 434, and an antenna portion 436. The monitoring device 430 may be constructed as an industrial product such that it can be installed in any environment. The monitoring device 430 may be contained in a case made of durable plastic, metal, or other suitable substance. For example, the case may be manufactured, in whole or in part, from a suitable plastic, such as acrylonitrile butadiene styrene (ABS) plastic or 30% glass filled high density polyethylene (HDPE) with carbon black to block ultra-violet (UV).

The case may be in multiple parts such that the individual components are contained in separate sections. This modular design enables easy assembly and serviceability. The case may comprise weep holes in the outer surface of the case to prevent freezing water from cracking/rupturing the case. In examples, the case may be keyed for easy assembly, and one size screw may be used for uniformity.

The case may also be manufactured to comprise a relief and bolt hole on a top portion. The relief and bolt hole provide the ability to use a crowbar or other suitable device to lift the monitoring device 430 from a flush mount installation. The relief and bolt hole also provide the ability to fasten the monitoring device 430 in place, such as with a bolt, to prevent the monitoring device 430 from moving.

In examples, the monitoring device 430 may be installed in a pit in a roadway, such that a surface of the monitoring device 430 sits flush with the surface of the roadway. This enables automobiles to pass the roadway without receiving interference from the monitoring device 430. The construction of the monitoring device 430 may enable the monitoring device 430 to withstand the pressure and force caused by automobiles, trucks, and other items from passing on top of the monitoring device 430 such that the monitoring device 430 remains unaffected. Additionally, the potting material such as epoxy or other suitable material encasing the individual components of the monitoring device 430 protects the individual components from adverse elements, such as water, ice, dirt, dust, and the like.

Figure 5:
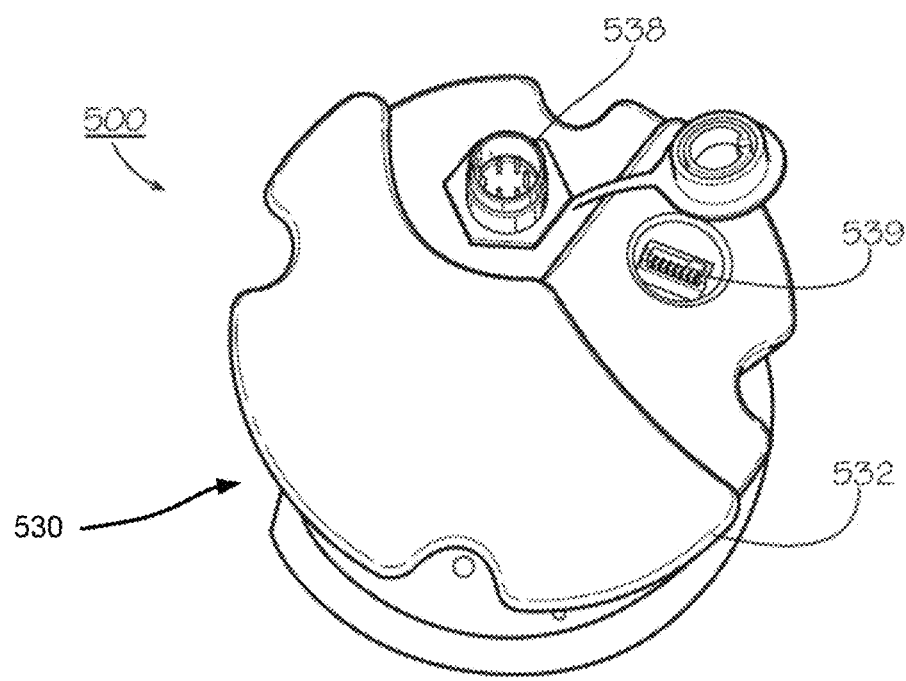
FIG. 5 illustrates an inverted perspective view of a monitoring assembly according to examples of the present disclosure.

FIG. 5 illustrates another assembled view of a monitoring assembly 500, including monitoring device 530 according to examples of the present disclosure. The parameter sensing portion 532 is shown as having a sensor port 538 for connecting a sensor and a service port 539 for connecting a service device, such as for maintenance. In the example illustrated in FIG. 5, the sensor port 538 is recessed such that a connecting cable for a sensor may be attached without interfering with the flat nature of the design of the parameter sensing portion 532. In examples with the parameter sensing portion 532 making up the bottom of the monitoring device 530, this recession enables the monitoring device to be set on a flat surface without the sensor cable interfering. In examples, the service port 539 may be omitted and the monitoring device 530 may be serviced remotely via the communication techniques discussed herein.

Figure 6:
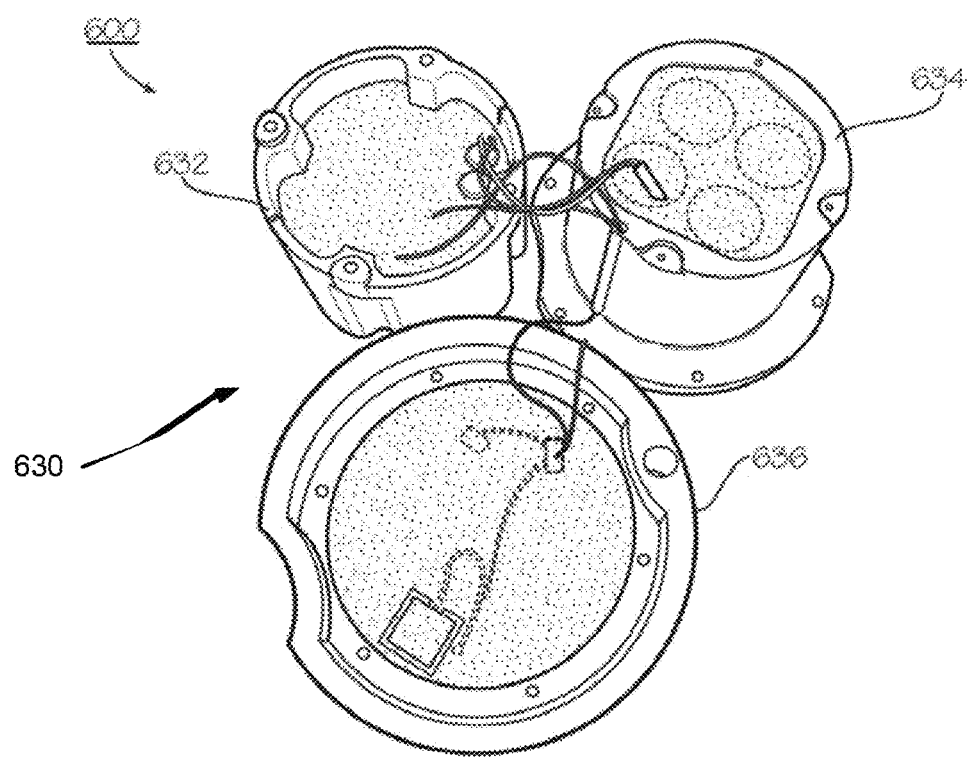
FIG. 6 illustrates a disassembled view of a monitoring assembly according to examples of the present disclosure.

FIG. 6 illustrates a disassembled view of a monitoring assembly 600 according to examples of the present disclosure. The monitoring device 630 comprises a parameter sensing portion 632, a power supply portion 634, and an antenna portion 636.

Although FIG. 5 illustrates a monitoring device 530 with one sensor port 538, additional sensor ports may be implemented. FIG. 7 illustrates a circuit board 700 of a parameter sensing portion (e.g., sensing portion 632) having one sensor port 738 according to examples of the present disclosure. FIG. 8 illustrates another circuit board 800 of a parameter sensing portion having five sensing ports 838a-e according to examples of the present disclosure. It should be understood that various other numbers of sensor ports may be implemented in various examples.

FIGS. 9-15C represent screenshots 900-1500C of a system for configuring and managing a monitoring device, such as monitoring device 130 of FIG. 1, monitoring device 230 of FIG. 2, and other monitoring devices as disclosed herein according to examples of the present disclosure. The system for configuring and managing the monitoring device (or monitoring devices) may be configured to execute on a computing system such as computing system 120 of FIG. 1 and/or computing system 320 of FIG. 3. The screenshots 900-1500C may be generated by the computing system when the computing system executes computer executable instructions configured to generate the screenshots.

Figure 9:
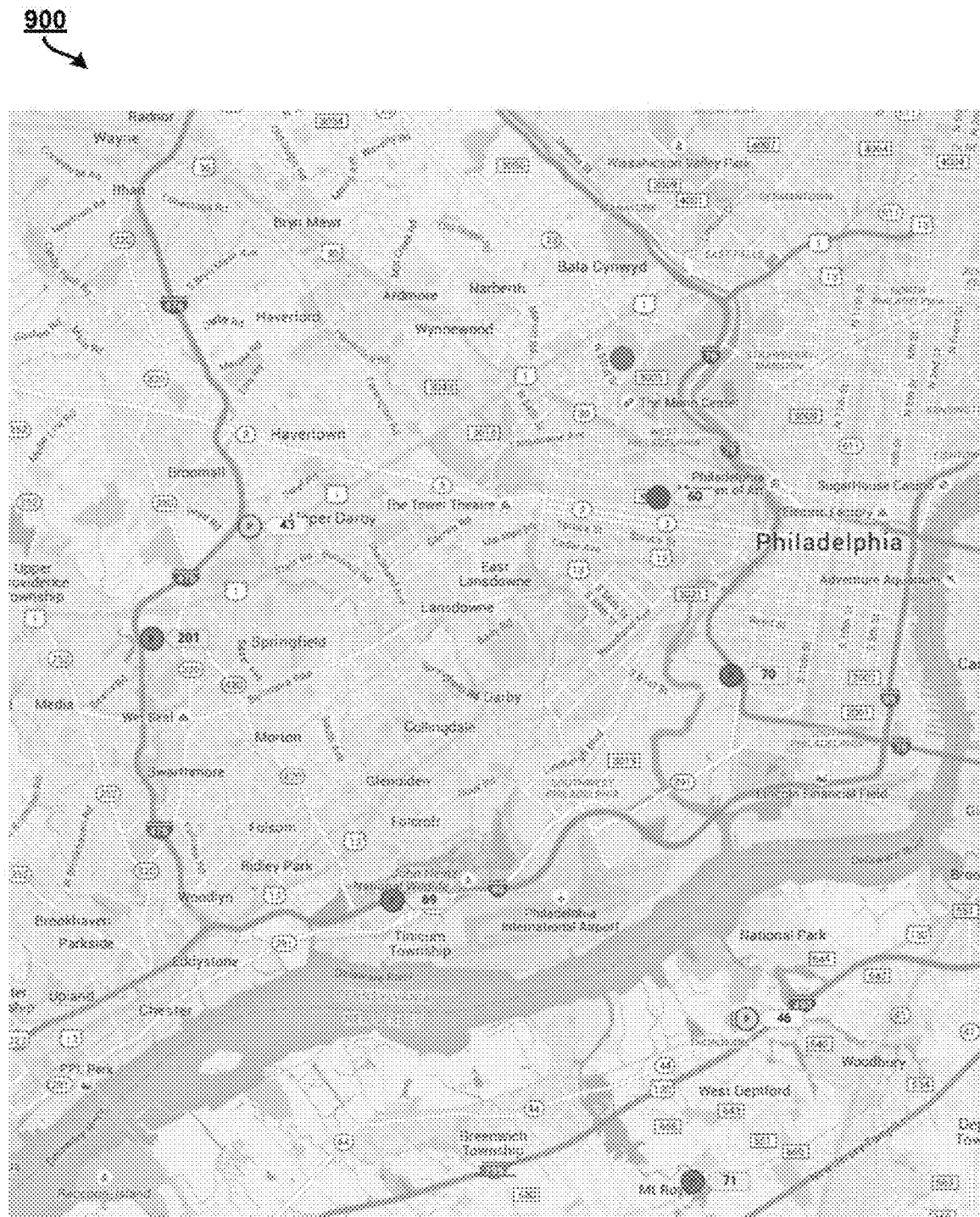
Figure 10:
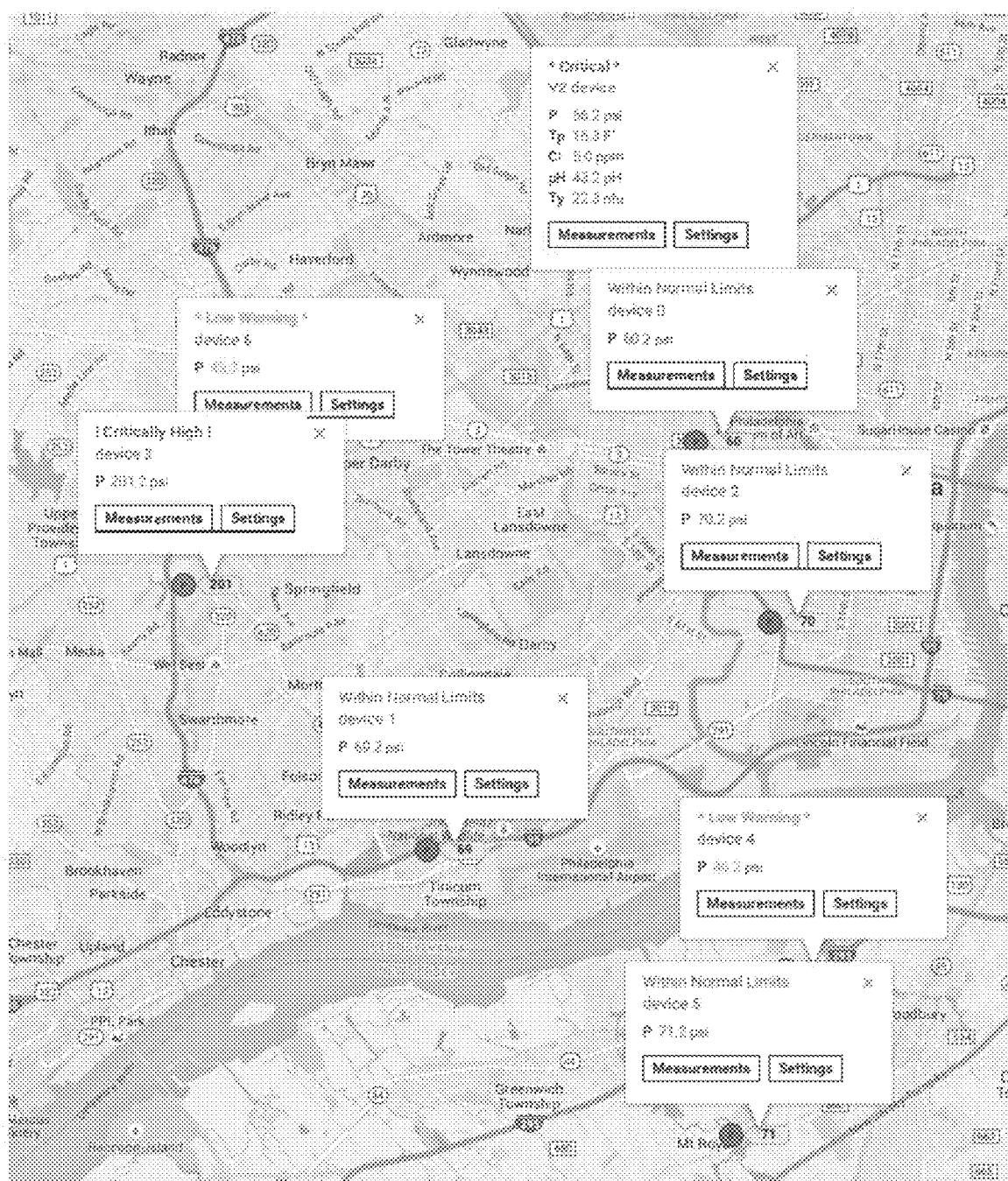

FIGS. 9 and 10 illustrate screenshots 900 and 1000 respective of a map of multiple monitoring devices over a geographic area. The monitoring devices are illustrated by dots. A dot represents a multi-parameter monitoring device and a dot with P represents a pressure monitor (single parameter monitoring device). In examples, an indicia may be used to indicate the status of the monitoring devices. As illustrated, red, yellow, and green dots represent as follows: red=if any one parameter is critical; yellow=if any one parameter is warning (such as low or high); green=no parameters are warning or critical. FIG. 10 illustrates a screenshot 1000 showing additional details for each of the monitoring devices including the current readings for each sensor for each monitoring device.

FIG. 11 illustrates a screenshot 1100 of a table of the monitoring devices of FIGS. 9 and 10. The table comprises the sensor reads for each sensor connected to each of the monitoring devices. In the example of FIG. 11, device 0 through device 6 represent single parameter (pressure) monitoring devices, while V2 device represents a multi-parameter monitoring device measuring turbidity, temperature, pressure, pH, and chlorine values.

Figure 12A:
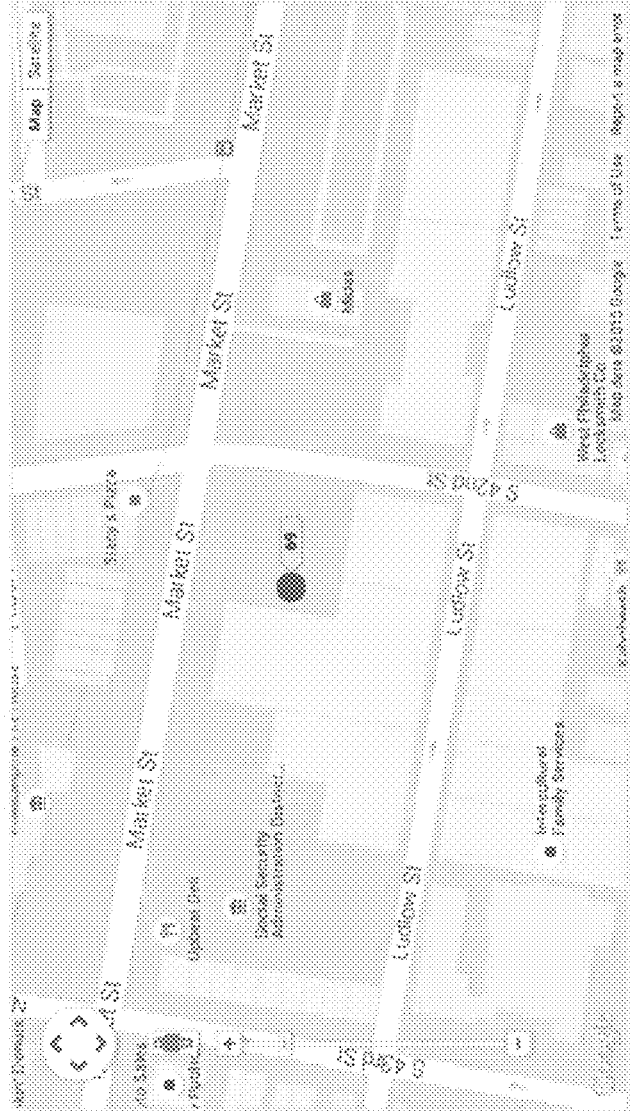
Figure 12B:
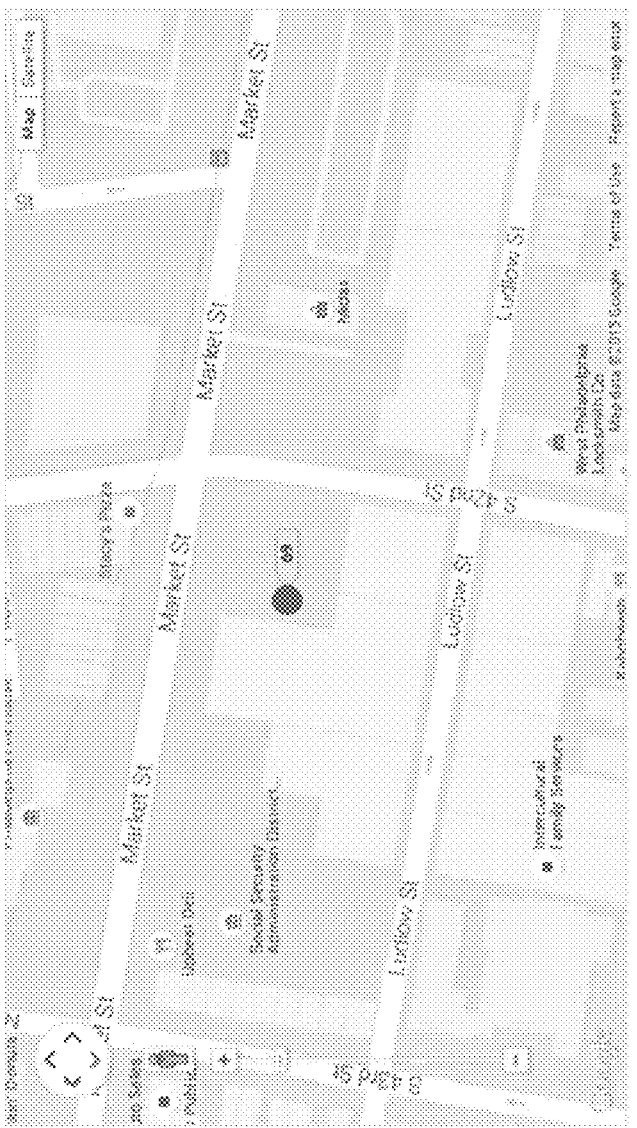
Figure 13A:
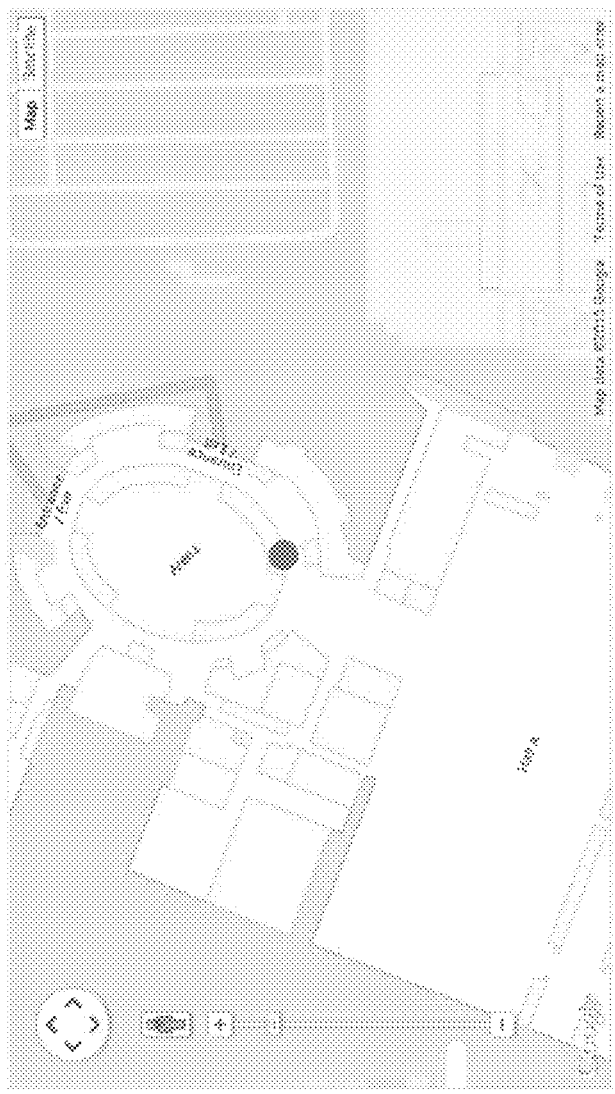
Figure 13B:
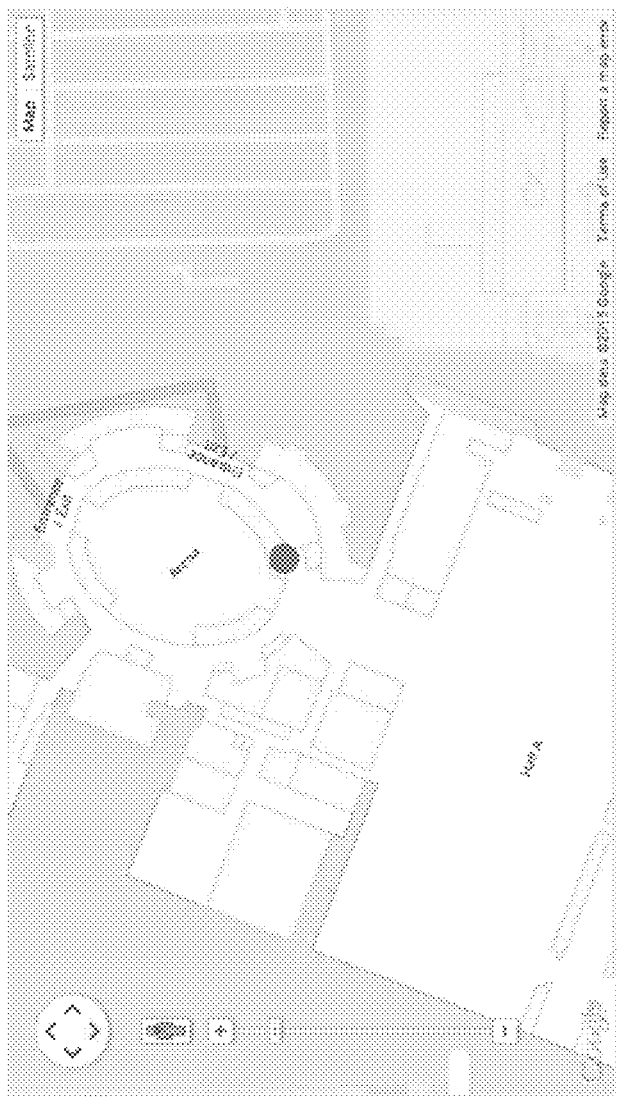
Figure 13B:
Figure 13B:
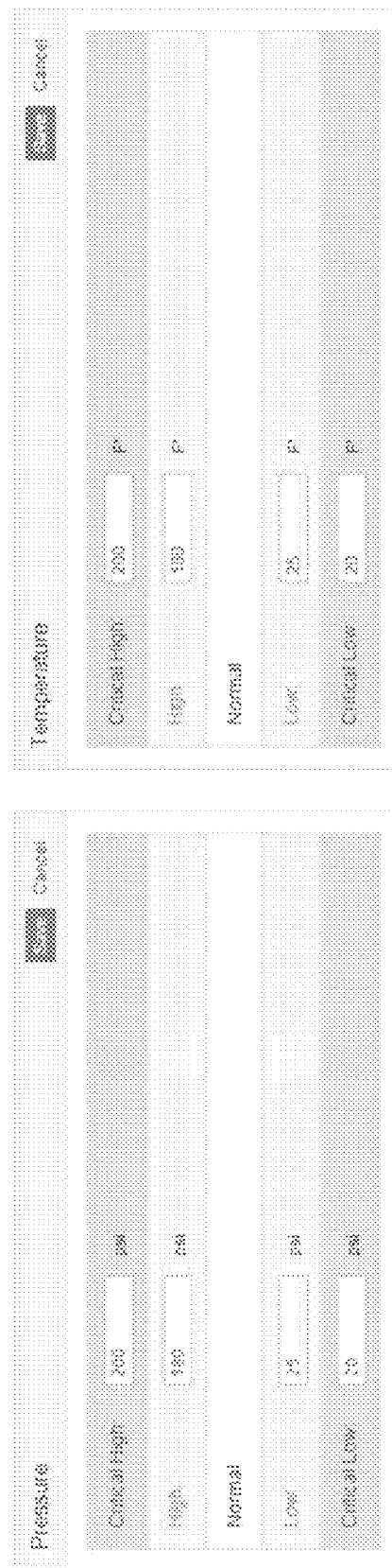

FIGS. 12A and 12B illustrate screenshots 1200A and 1200B of a configuration screen for a single parameter monitoring device. A map illustrates the geographic position of the monitoring device.

Additionally, various configuration options are available, including description, mode, status, auto GPS, latitude/longitude, elevation, uploads per day, and unit ID. The auto GPS enables a GPS in the monitoring device to automatically determine the longitude, latitude, and/or elevation of the pressure monitor. In examples, these values may be manually entered, as may the rest of the configuration options. To edit the monitoring device settings, click on edit, change the values accordingly, then click on Save. A brief description of the Settings fields are given below:

Description: Each monitoring device can be given a description name. The description can be used as a way to identify monitoring device without having to reference the monitoring device ID. Street addresses could be used as an example.

Mode: Selecting "Request Maintenance Mode" will set the monitoring device into maintenance mode after the next upload occurs by the monitoring device unit. This may take up to 24 hours. Once in maintenance mode, any configuration changes made to the unit will take affect within minutes in some examples.

Status: This field reports the current pressure range that the monitoring device is in (i.e., Normal, Warning, or Critical).

Latitude and Longitude: These fields are automatically filled when the monitoring device is initially installed if the monitoring device receives a strong GPS satellite signal.

Elevation: This field is entered in manually in some examples or may be entered automatically in others.

Uploads Per Day: This field indicates how many uploads should be performed by the monitoring device daily. For example, 12 would result in the monitoring device uploading every 2 hours, 6 would produce an upload every 4 hours, and so on. Note: The recommended Uploads Per Day interval is 1 (i.e. one upload per day).

Monitoring Device ID: This is the unique identifier for the monitoring device. In some examples, this field cannot be changed.

FIGS. 13A-13D illustrate screenshots 1300A-1300D of a configuration screen for a single parameter monitoring device. Like the configuration screen for the single parameter monitoring device, multiple configuration options are available. As also illustrated, thresholds may be set for critical high, high, low, and critical low values for pressure, temperature, pH, turbidity, and chlorine. The Pressure Sensor range allows users to be notified when pressure is entering or exiting a certain pressure range. Three ranges are used: Normal, Warning, and Critical (with high and low bounds for Warning and Critical). In examples, when two consecutive measurements are taken for any range, the pressure sensor automatically uploads the data and users registered to receive alerts are notified.

Additionally, a flush schedule indicates when a solenoid connected to the monitoring device may be activated to cause the fluid distribution system to perform a flushing operation. In the present example, flushing may occur when any of the following occur: if pressure is higher than 4 PSI; if temperature is higher than 4° F.; if temperature is lower than 3° F.; if chlorine is lower than 3 ppm; if acidity is higher than 3 pH; or if turbidity is higher than 5 nephelometric turbidity units (NTU).

Figure 14A:
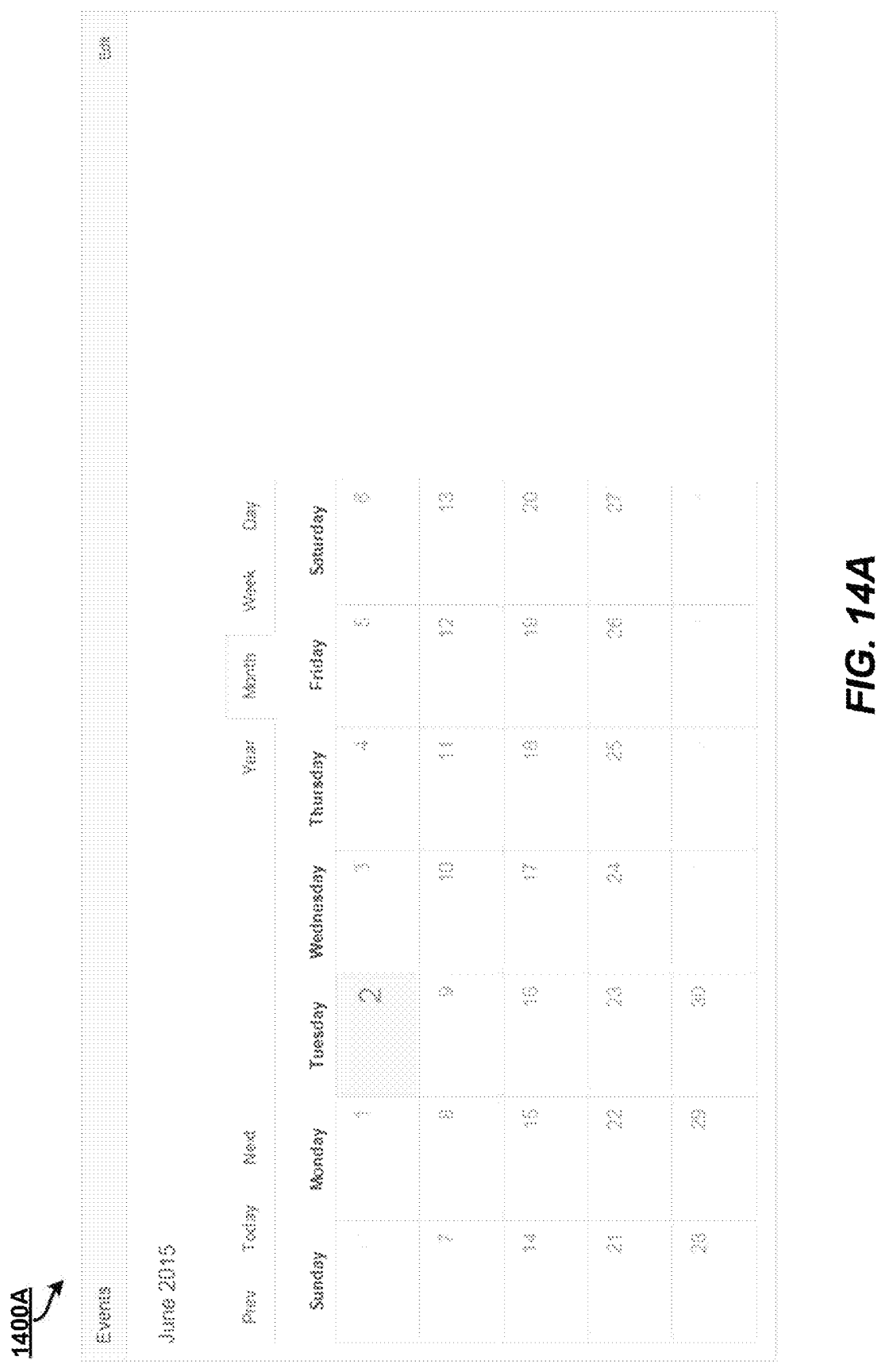
Figure 14B:
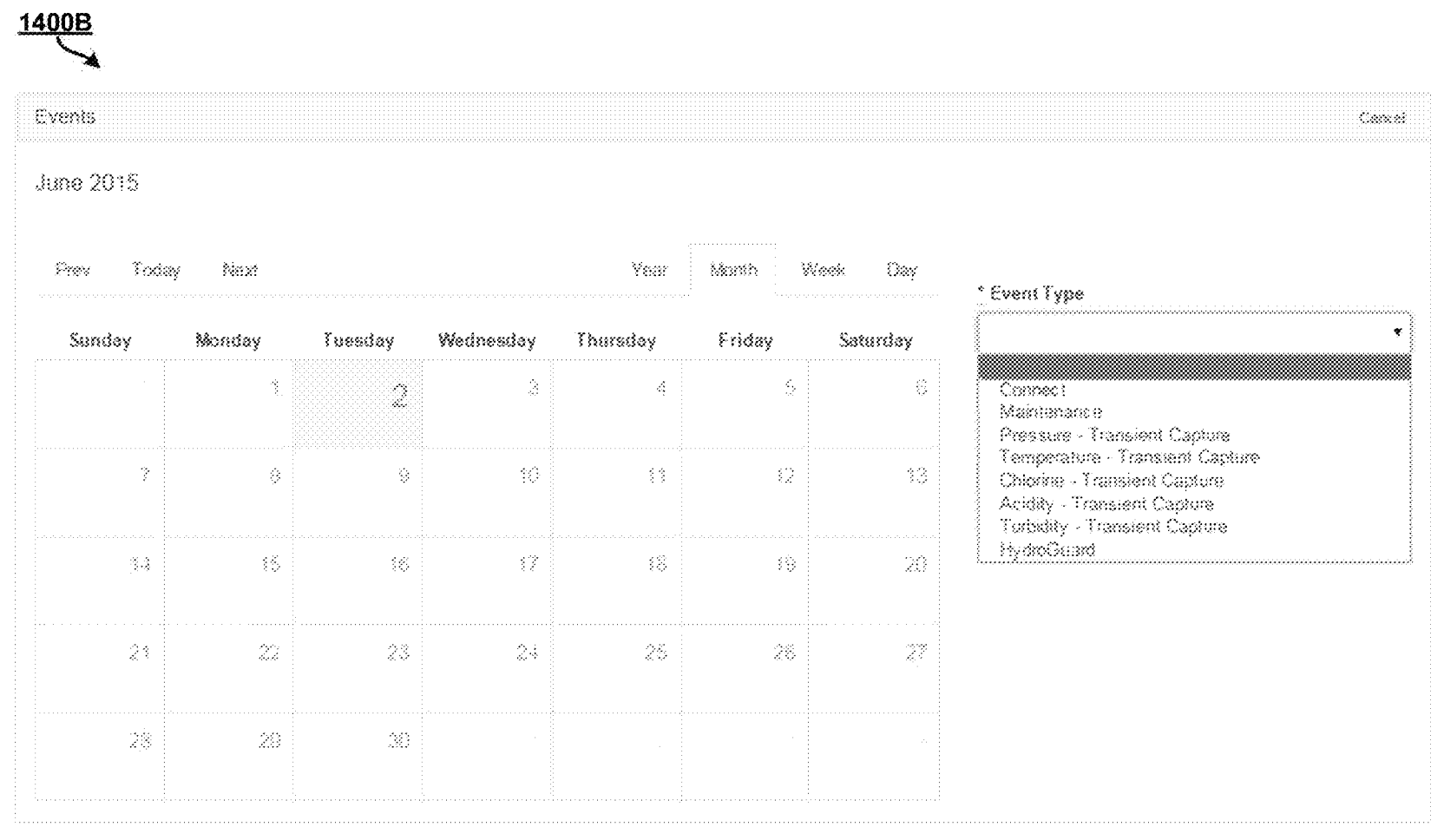
Figure 14C:
Figure 14C:
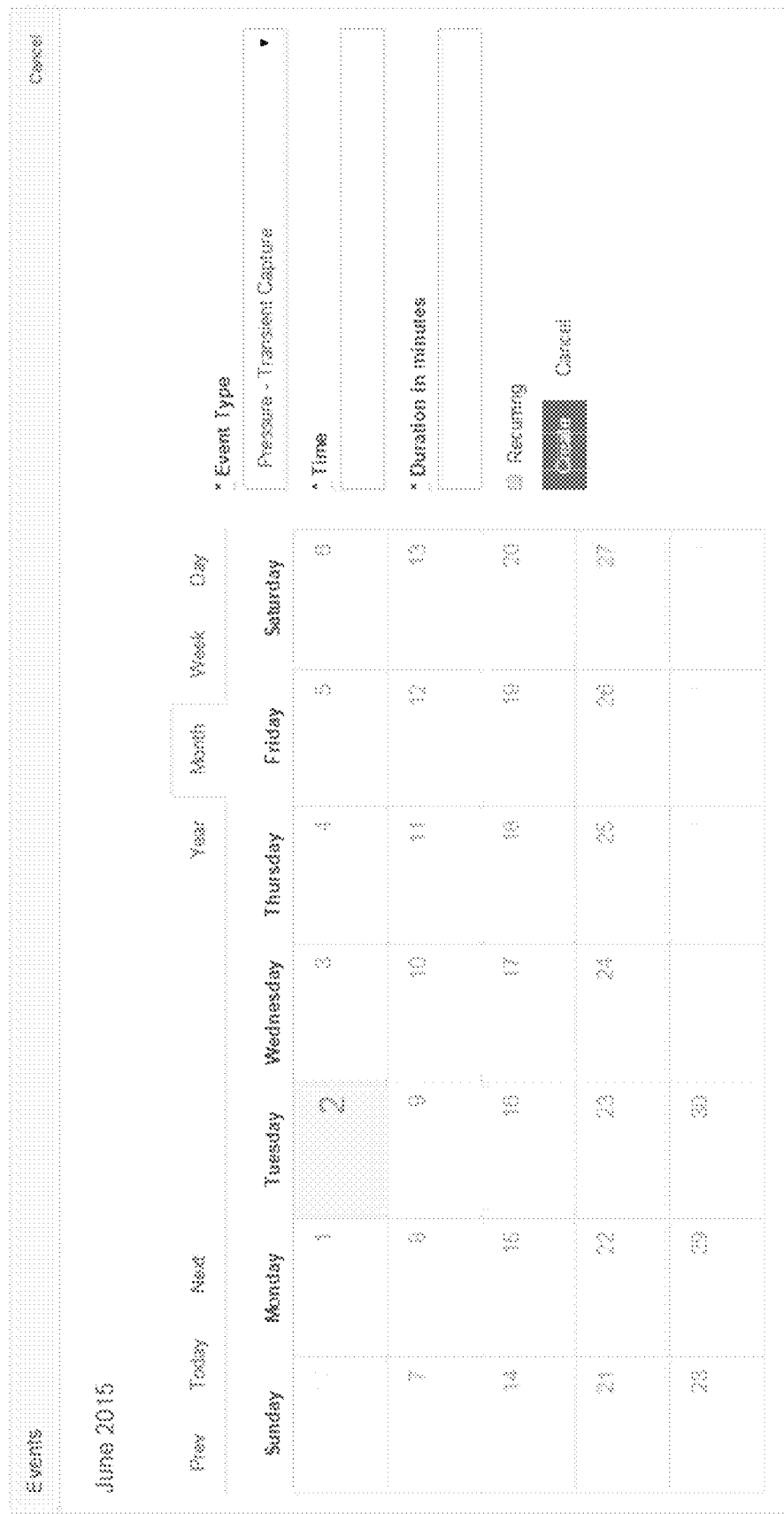
Figure 19:
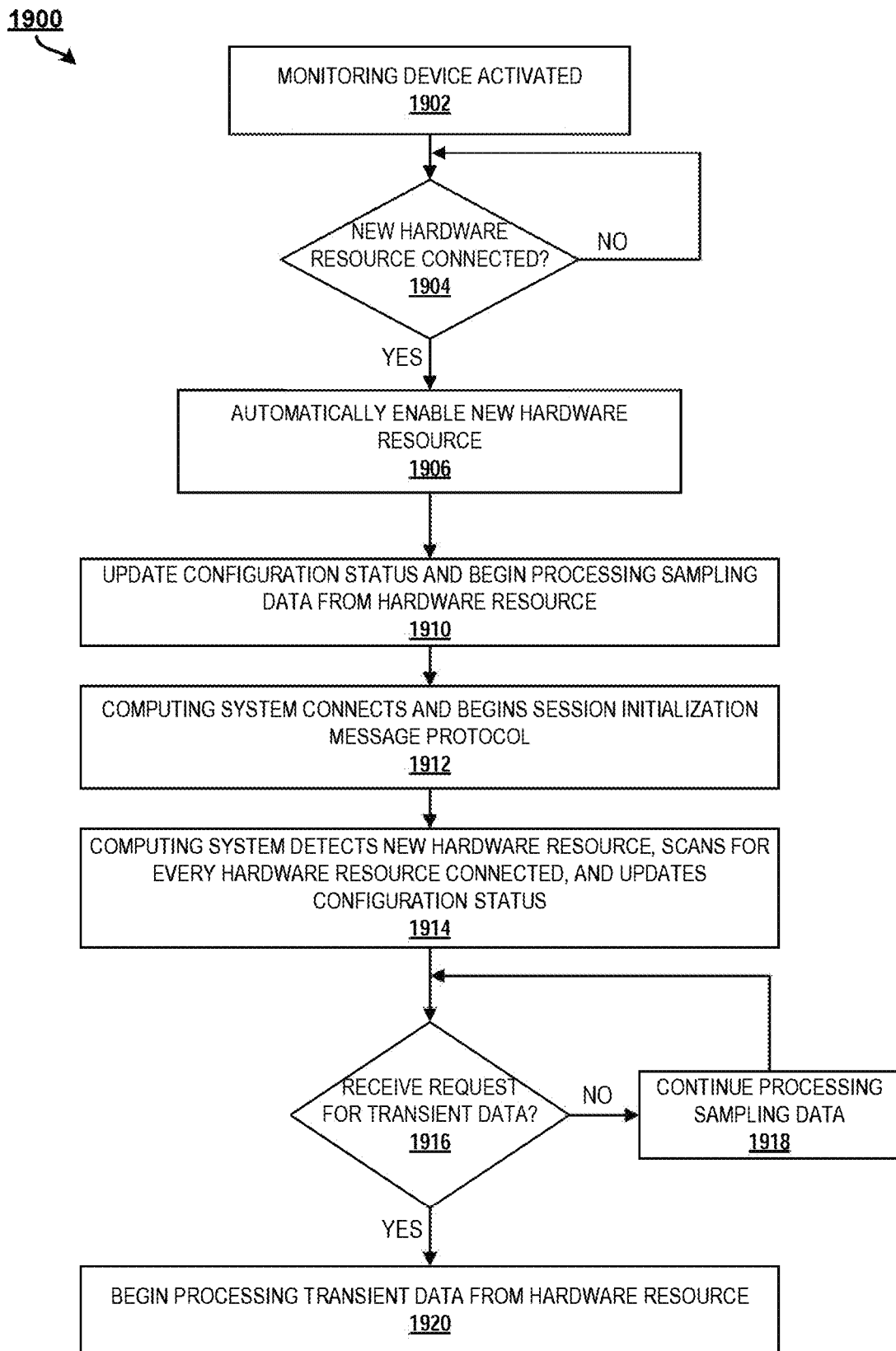
FIG. 19 is a flow diagram illustrating a method for processing acoustic signals, according to examples of the present disclosure.

FIGS. 14A-14C illustrate screenshots 1400A-1400C of a calendar of events and event setup options. The events may capture transient data readings of pressure, temperature, chlorine, acidity (pH), and turbidity for example, or may cause events to occur such as flushing of the fluid distribution system, connection of the monitoring device, and maintenance of the monitoring device. The capturing and processing of transient data is discussed further below, and as shown in FIG. 19.

Figure 15A:
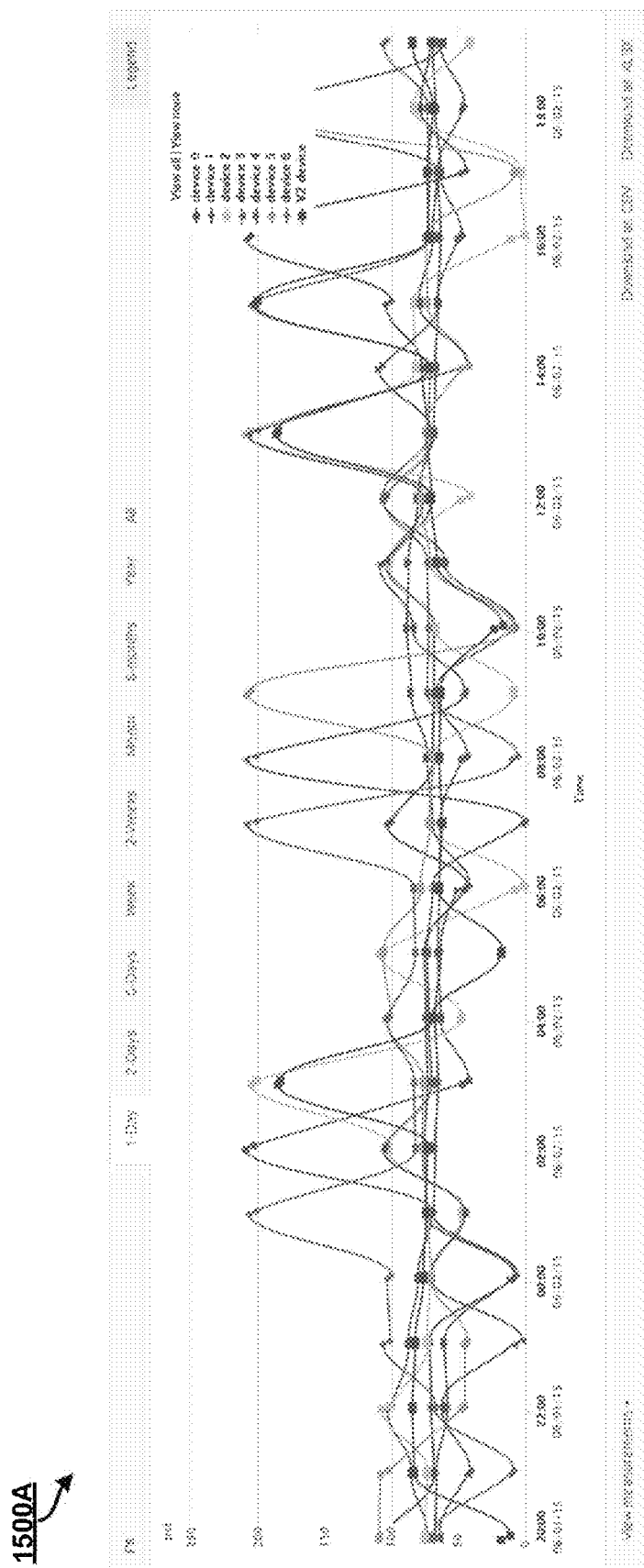
Figure 15B:
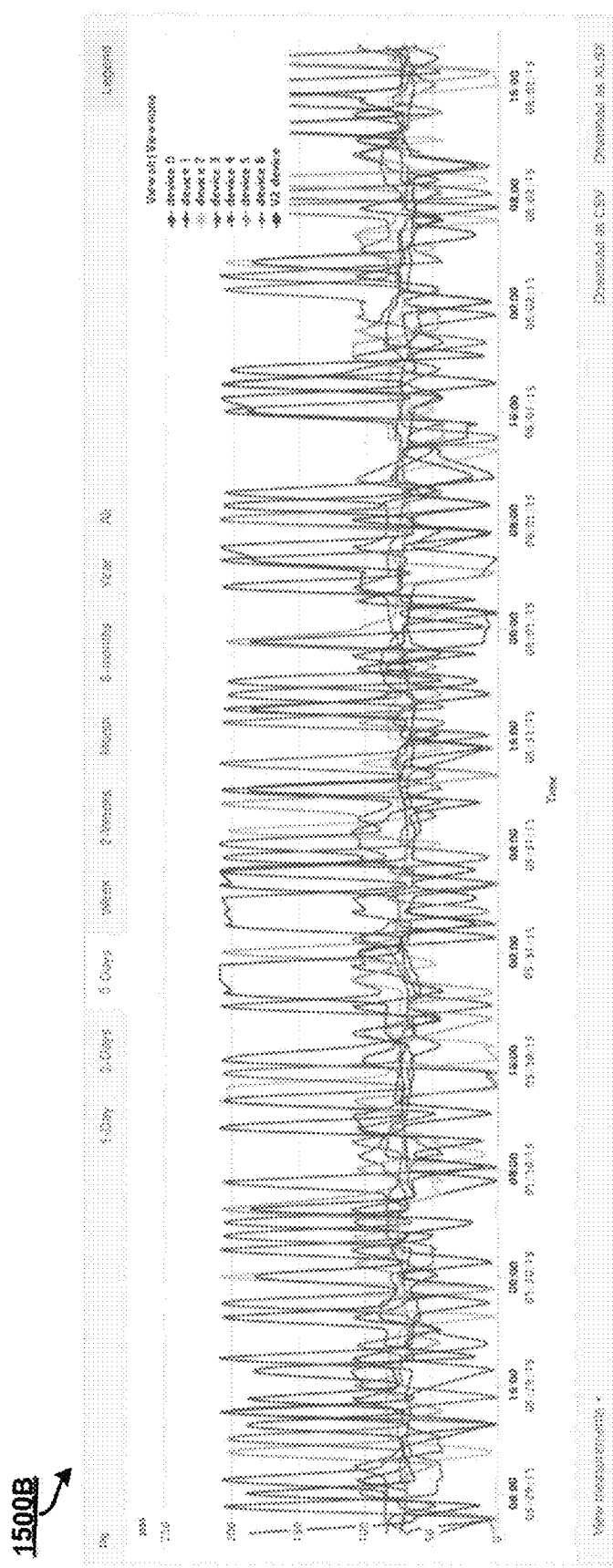
Figure 15C:

FIGS. 15A-15C illustrate screenshots 1500A-1500C of graphs plotting the monitored parameters. In the case of FIG. 15A, device 0 through device 6 and V2 device are illustrated on the same graph over a one day period. FIG. 15B illustrates a graph of the same devices over a five day period. The graphs may be viewed over different periods, such as one day, two days, five days, week, two weeks, month, six months, year, and all time. FIG. 15C illustrates a graph of chlorine for V2 device, for example, over a one day period. Any parameter may be displayed individuality, and devices may be viewed individually or multiple devices may be displayed together. These graphs are merely examples.

The graphs may contain the collected data gathered by the monitoring devices belonging to a client's organization. Data can be viewed within a specified time frame, both, graphically and by downloading the data as a comma-separated values (CSV) or Microsoft Excel® open extensible markup language (XML) format spreadsheet (XLSX) file to be viewed in any spreadsheet program. The collected measurements are represented on the graph with the y axis being psi (or ppm for chlorine levels) and the x axis being the time that the measurement was taken. Each monitoring device belonging to the client's organization is represented by a different colored line, for example. The Legend button (located in the upper right section of the graph in FIG. 15A for example) displays the monitoring device to color-coding mapping currently being used. Clicking on Legend allows the user to select and de-select monitoring device to be displayed. Clicking on any of the lines within the graph may navigate to a page to view data collected by the individual monitoring device selected. In examples, Users can zoom in and out of the graph.

Figure 16:
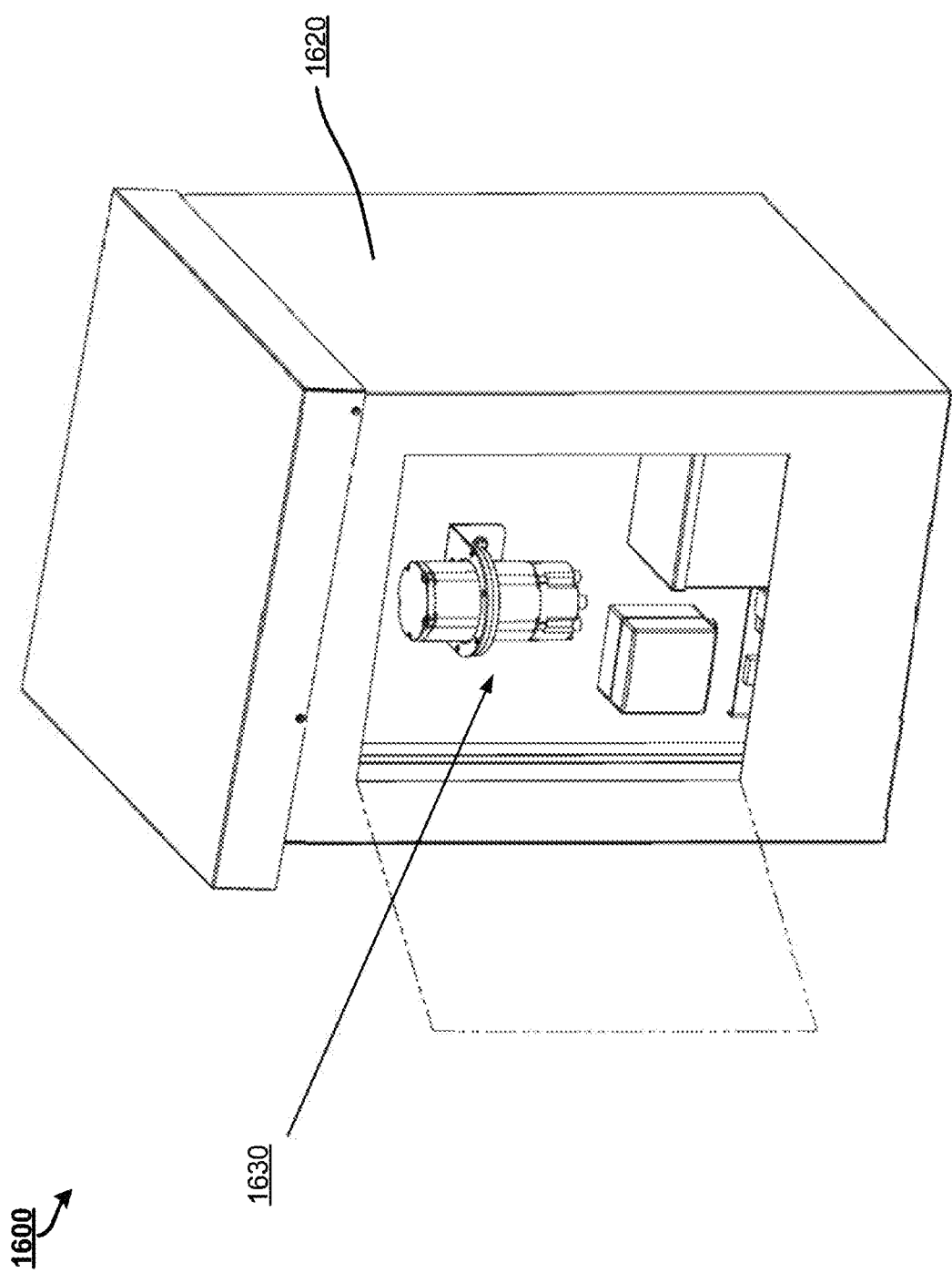
FIG. 16 illustrates another assembled view of a monitoring assembly according to examples of the present disclosure.

FIG. 16 is diagram of a monitoring assembly 1600, according to various examples of the present disclosure. As seen in FIG. 16, a monitoring device 1630 can be mounted within an enclosure 1620. Enclosure 1620 to houses equipment, such as monitoring device 1630, and may provide protection from vandalism or the environment. Enclosure 1620 is designed for extended life and performance of the monitoring device 1630. In some examples, enclosure 1620 may be UV and impact resistant polyethylene and provide lockable solutions for a wide range of utility applications. In some examples, enclosure 1620 may be a metal housing made of high-strength aluminum.

Figure 17:
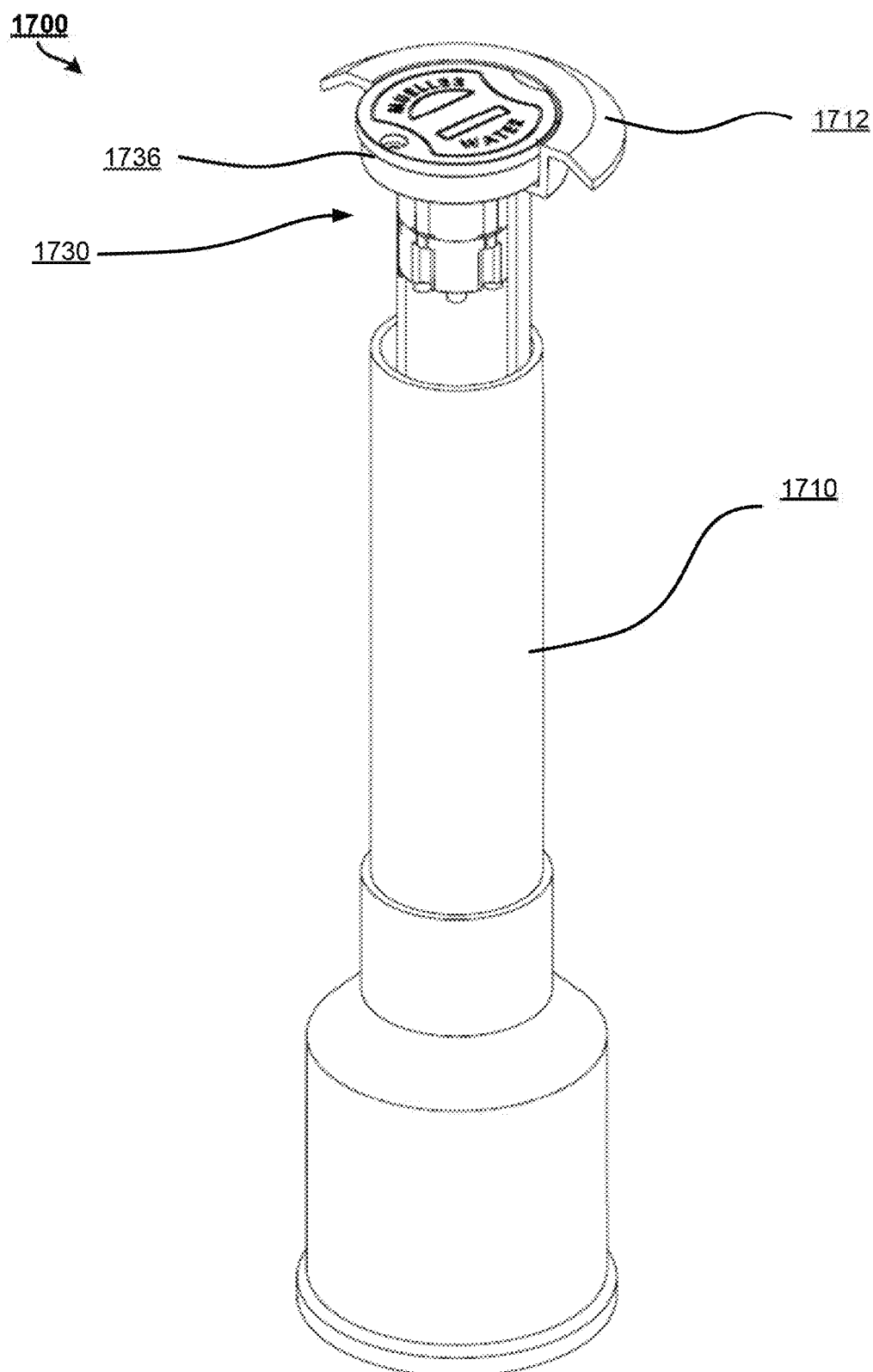
FIG. 17 illustrates a partial cross-sectional side view of a monitoring assembly, according to examples of the present disclosure.

FIG. 17 is partially cutaway side view of a monitoring assembly 1700, according to various examples of the present disclosure. As seen in FIG. 17, the monitoring assembly 1700 comprises a monitoring device 1730 and a valve box 1710. To communicate data and receive orders, the monitoring device 1730 comprises an antenna portion 1736, such as antenna portion 436 and antenna portion 636, as discussed herein for FIGS. 4 and 6, respectively. The antenna portion 1736 is mounted to an adjustable top 1712. The adjustable top 1712 connects to the valve box 1710, forming an enclosure extending from a ground surface to the top of a pipe to protect the enclosed monitoring equipment. The adjustable top 1712 can be adjusted telescopically to vary the overall height of the monitoring assembly 1700, based on the depth of the pipe below ground level. Other sensors may be used with monitoring assembly, such as pressure, temperature, turbidity, pH, chlorine, and flow sensors.

Figure 18:
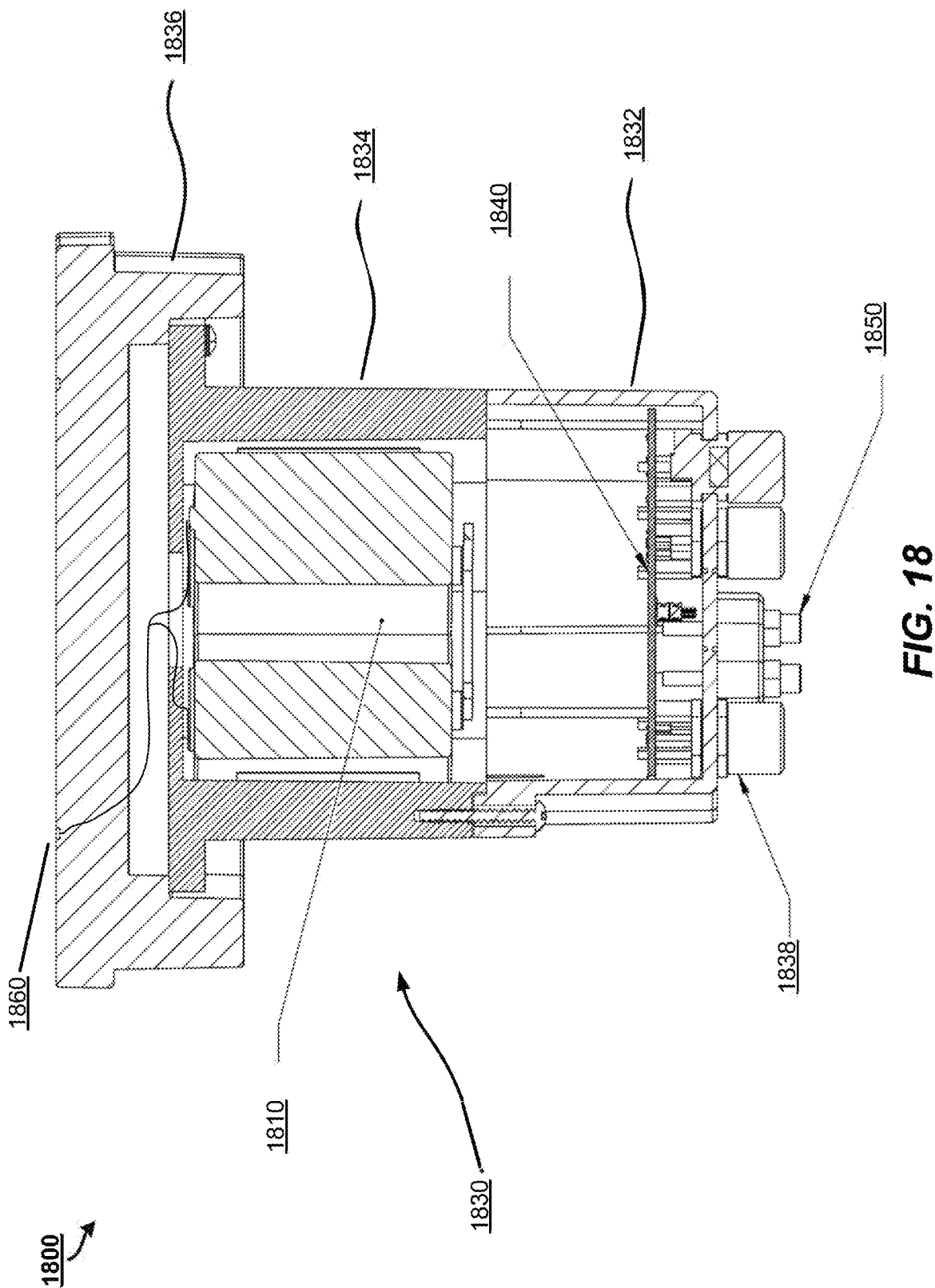
FIG. 18 illustrates a cutaway side view of a monitoring assembly, according to examples of the present disclosure.

FIG. 18 is a cutaway side view of a monitoring assembly 1800, according to various examples of the present disclosure. The monitoring assembly 1800 comprises an antenna portion 1836. The monitoring assembly 1800 also comprises a battery portion 1834 enclosing a battery pack 1810. Extending from a lower end of the battery portion 1834 is the sensing portion 1832 enclosing a circuit board 1840, such as circuit board 700 and circuit board 800, as discussed herein for FIGS. 7 and 8, respectively. In various examples, the antenna portion 1836 may comprise an auxiliary power input 1860. The auxiliary power input 1860 may be connected to the battery pack 1810 by a wire, so that the battery pack 1810 may be recharged by another power source, such as a portable battery pack. The auxiliary power input 1860 may comprise a waterproof connector to prevent corrosion over the life of the monitoring device 1830 and the auxiliary power input 1860.

FIG. 19 is a process flow diagram illustrating an embodiment of a method 1900 for capturing and processing transient data. In this embodiment, the method 1900 comprises the step of activating a monitoring device/assembly, as indicated in step 1902. The monitoring device/assembly may comprise the monitoring device 230 shown in FIG. 2, or in some examples, may comprise any of the monitoring devices described herein. In the example embodiment, activation may be accomplished by turning on the monitoring device 230 by a field engineer. In other examples the monitoring device 230 may be in a sleep mode, and step 1902 requires the computing system 320 to activate the monitoring device 230 with a software code.

The monitoring device 230 hardware is designed to handle and connect to a number of hardware resources based on configurable requirements. At step 1904, the monitoring device 230 continuously checks and determines when a new hardware resource, such as a sensor or a solenoid, is connected. According to some examples, the hardware resources of the monitoring assembly may comprise a pressure sensor, a temperature sensor, a turbidity sensor, a pH sensor, and a chlorine sensor, either all integrated into one sensor, or combined in separate sensors. The sensors may operate continually to provide the sampling and transient data.

The hardware resource is automatically enabled by the monitoring device 230 at step 1906. The monitoring device 230, at step 1910, updates its configuration status and begins to process sampling data from the hardware resource. The monitoring device 230 may communicate the hardware change during the next session initialization message. The computing system 320 connects to the monitoring device 230 at step 1912, and begins a session initialization message protocol. If the session initialization message indicates the change in hardware, the computing system, at step 1914, detects the new hardware resource, scans through the updated monitoring device 230 configuration and every hardware resource, and updates its status.

In some examples, the monitoring device 230 may have a sensor resource class for each physical sensor. The sensor resource class is a generic interface definition to handle multiple sensor types with a common interface. Sensor resources, as described herein, can handle sampling data and transient data. Sampling data may refer to sample parameters at relatively slow rate and keeps average, maximum and minimum of every hour. Sampling data may comprise several configurable parameters such as a sampling interval and period. The sampling interval may comprise a time span between samples, in seconds. The monitoring device 230 may drop samples and only keep the minimum and maximum for a period. A period is a period of time for minimum and maximum samples in seconds. In the example embodiment, the default is 3600 seconds.

Transient data may comprise samples processed at a high rate, and the monitoring device 230 or computing system 320 compresses the data. Transient data may comprise several configurable parameters such as transient interval and tolerance. Transient interval is an exponent for power of base 2 of time between samples in 1/4096 seconds. In the example embodiment, the default transient interval is 5 for a 1/128 second period. Tolerance is the minimum delta required for a sample to be recorded, recorded in raw analog-to-digital converter (ADC) conversion units. For an ADC, the most popular convention is to draw a straight line through the mid-points of the codes, or the code centers. If the sample is less than the delta from the straight line, it is dropped.

The computing system 320 may allow the parameters of the data, and the rates that the data is captured, to be changed based on predetermined criteria defined by the user. In some examples, sensor actions are used by the computing system to define the transient and sample data parameters. Sensor actions may comprise a start time and duration during which the monitoring device 230 will take transient measurements.

In the example embodiment, during the transient data process of step 1920, the monitoring device 230 does not keep the state of the data. Instead, it is the responsibility of the computing system 320 to keep the state of the data. After the monitoring device 230 responds with data, the data remains recoverable till the computing system 320 instructs the monitoring device 230 to permanently delete the data by a delete action. If the session unexpectedly ends after the samples of data are sent to the server but the monitoring device 230 does not get a request to delete the sent data, the monitoring device 230 will automatically recover the data.

In some examples there may be action resources which may handle scheduling of transient data monitoring of the corresponding sensor(s). These actions require the start time and the duration. The action is a sub-resource of multiple types of resources with a purpose of scheduled actions with or without duration. An example of an action with duration is flushing, which requires duration. An example of an instantaneous action is connection to the server because it does not have a duration requirement.

In another example embodiment, the computing system 320 may level load connect actions by choosing the least busy time for connection within the next hour of each "Wake Up" action, and schedule the exact time for the monitoring device 230. For example, the user may schedule an upload action at 9:00am. The computing system 320 scans actions of the monitoring device 230 that upload between 9:00am and 10:00am and builds a frequency chart. The computing system 320 chooses the least busy time within that hour and sets the action for that time, for example, 9:01:13am. The next time the monitoring device 230 connects, the computing system 320 posts the Wake Up action at 9:01:13am to the monitoring device 230.

Figure 20:
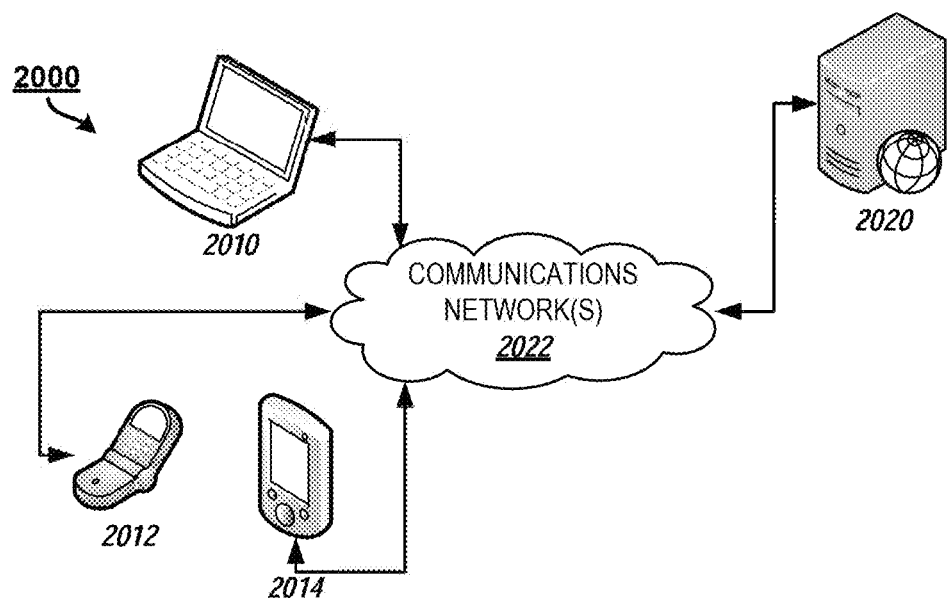
FIG. 20 is a block diagram of a parameter sensing system, according to examples of the present disclosure.

FIG. 20 is a block diagram of a parameter sensing system 2000 according to various implementations of the present disclosure. The parameter sensing system 2000 comprises one or more user devices, such as user devices 2010, 2012, and 2014, and a parameter sensing server 2020. These and other systems are capable of interacting and communicating via one or more communication network(s) 2022. The user devices 2010, 2012, 2014 may comprise mobile devices such as smart phones, including iPhones, BlackBerries, and Android-based devices, application-enabled mobile phones, personal computers, etc. The communication network(s) 2022 may represent telephone lines, such as land line or public switched telephone network (PSTN) systems, mobile phone channels and systems, communication channels for exchanging data and information, such as a local area network (LAN), wide area network (WAN), and/or other data, communication, or telecommunication networks that collectively make up the Internet. In some examples, any communication network(s) 2022 that support the TCP/IP protocol may be utilized.

Figure 21:
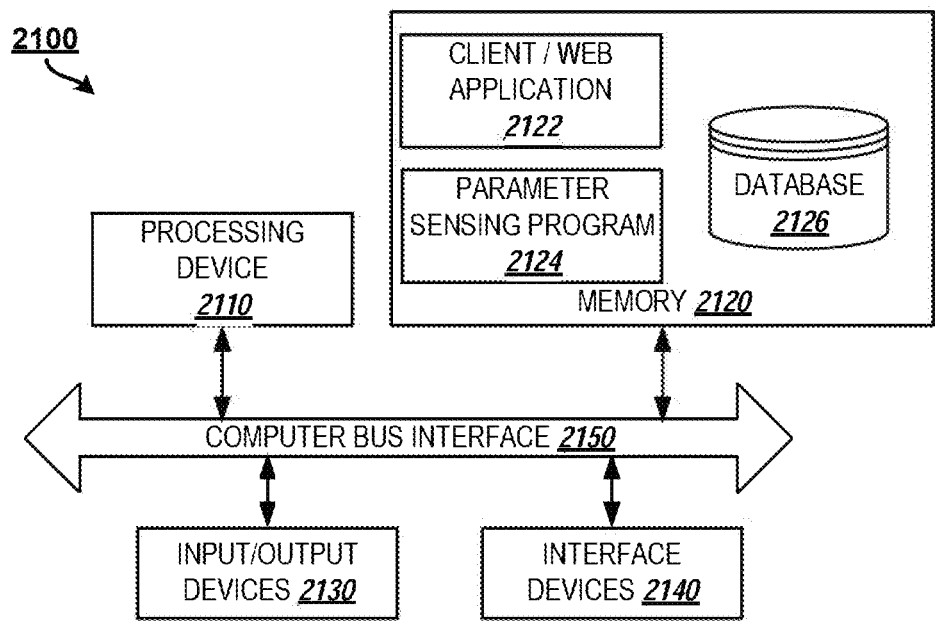
FIG. 21 is a block diagram illustrating a computer architecture for computing devices described herein as part of the parameter sensing system, according to examples of the present disclosure.

FIG. 21 is a block diagram illustrating an embodiment of a computer system 2100 utilized in the parameter sensing system 2000, according to various implementations of the present disclosure. The computer system 2100 may represent a user device 2010, 2012, 2014, the parameter sensing server 2020 shown in FIG. 20, or another computer system comprising the systems described herein or for performing the methods described herein. As shown in this embodiment, the computer system 2100 comprises a processing device 2110 and a memory device 2120. The memory device 2120 may comprise a client/web application 2122, a parameter sensing program 2124, a database 2126, and/or the like. The computer system 2100 further comprises input/output devices 2130 and interface devices 2140. The components of the computer system 2100 are interconnected and may communicate with each other via a computer bus interface 2150 or other suitable communication devices. The parameter sensing program 2124 may perform the same functions as the parameter sensing module 232, as described herein for FIG. 2, and vice versa.

In some examples, each component of the computer system 2100 as shown may comprise multiple components on multiple computer systems of a network. For example, the computer system 2100 may comprise servers, such as application servers, file servers, database servers, web servers, etc., for performing various functions described herein. The servers of the computer system 2100 may for example be physically separate computer servers or virtual servers in a VMware ESXi 4.0 virtual environment, among other implementations.

The processing device 2110 may be one or more general-purpose or specific-purpose processors, microcontrollers, or microprocessors for controlling the operations and functions of the parameter sensing server 1210. In some implementations, the processing device 2110 may comprise a plurality of processors, computers, servers, or other processing elements for performing different functions within the computer system 2100.

The memory device 2120 may comprise one or more internally fixed storage units, removable storage units, and/or remotely accessible storage units, each including a tangible storage medium. The various storage units may comprise any combination of volatile memory and non-volatile memory. For example, volatile memory may comprise random access memory (RAM), dynamic RAM (DRAM), etc. Non-volatile memory may comprise read only memory (ROM), electrically erasable programmable ROM (EEPROM), flash memory, etc. The storage units may be configured to store any combination of information, data, instructions, software code, etc. The client/web application 2122, the parameter sensing program 2124, the database 2126, and/or the like may be stored in one or more memory devices 2120 and run on the same or different computer systems and/or servers.

In addition to the memory device 2120, the computer system 2100 may comprise other computer-readable media storing information, data, instructions, software code, etc. It will be appreciated by those skilled in the art that computer-readable media can be any available media that may be accessed by the computer system 2100, including computer-readable storage media and communications media. Communications media comprises transitory signals. Computer-readable storage media comprises volatile and non-volatile, removable and non-removable storage media implemented in any method or technology for the non-transitory storage of information. For example, computer-readable storage media comprises, but is not limited to, RAM, ROM, erasable programmable ROM ("EPROM"), electrically-erasable programmable ROM ("EEPROM"), FLASH memory or other solid-state memory technology, compact disc ROM ("CD-ROM"), digital versatile disk ("DVD"), high definition DVD ("HD-DVD"), BLU-RAY or other optical storage, magnetic cassettes, magnetic tape, magnetic disk storage or other magnetic storage devices and the like. According to some examples, the computer system 2100 may comprise computer-readable media storing computer-executable instructions that cause the computer system to perform aspects of the method 1900 described herein in regards to FIG. 19.

The input/output devices 2130 may comprise various input mechanisms and output mechanisms. For example, input mechanisms may comprise various data entry devices, such as keyboards, keypads, buttons, switches, touch pads, touch screens, cursor control devices, computer mice, stylus-receptive components, voice-activated mechanisms, microphones, cameras, infrared sensors, or other data entry devices. Output mechanisms may comprise various data output devices, such as computer monitors, display screens, touch screens, audio output devices, speakers, alarms, notification devices, lights, light emitting diodes, liquid crystal displays, printers, or other data output devices. The input/output devices 2130 may also comprise interaction devices configured to receive input and provide output, such as dongles, touch screen devices, and other input/output devices, to enable input and/or output communication.

The interface devices 2140 may comprise various devices for interfacing the computer system 2100 with one or more types of servers, computer systems and communication systems, such as a network interface adaptor as is known in the art. The interface devices 2140 may comprise devices for communicating between the parameter sensing server 2020 and the user devices 2010, 2012, or 2014 over the communication network(s) 2022, for example. In some examples, the interface devices 2140 may comprise a network interface adapter or other hardware or software interface elements known in the art.

The client/web application 2122 may comprise a user application for facilitating the monitoring device(s) and the data captured from the one or more sensors, as described herein. In some examples, the client/web application 2122 may execute directly on a user device 2010, 2012, 2014 and interface with the parameter sensing server 2020 over the communication network(s) 2022. The client/web application 2212 may further represent a web-based application executing on the parameter sensing server 2020 or other web server and delivered to a web browser executing on the user devices 2010, 2012, 2014 over the communication network(s) 2022. The client/web application 2122 may be implemented in hardware, software, or any combination of the two on the user devices 2010, 2012, 2014, the parameter sensing server 2020, and/or other computing systems in the parameter sensing system 2000.

The parameter sensing program 2124 may comprise any suitable instructions for processing the sample and transient data from the one or more sensors connected to any one of the monitoring device(s) or monitoring assemblies described herein. For example, the parameter sensing program 2124 may receive any data from resource hardware of the parameter sensing system 2000 including at least pressure, pH, turbidity, temperature, chlorine, etc., as well as other fluid measurements known in the art, such as oxidation reduction potential (ORP), conductivity, resistivity, flow rate, etc. The parameter sensing program 2124 may be omitted from the parameter sensing server 2020 in some examples or placed in a separate processing system according to other examples. The parameter sensing program 2124 may be implemented in hardware, software, or any combination of the two on the user devices 2010, 2012, 2014, the parameter sensing server 2020, and/or other computing systems in the parameter sensing system 2000.

Other examples may comprise additional options or may omit certain options shown herein. One should note that conditional language, such as, among others, "can," "could," "might," or "may," unless specifically stated otherwise, or otherwise understood within the context as used, is generally intended to convey that certain examples comprise, while other examples do not comprise, certain features, elements and/or steps. Thus, such conditional language is not generally intended to imply that features, elements and/or steps are in any way required for one or more particular examples or that one or more particular examples necessarily comprise logic for deciding, with or without user input or prompting, whether these features, elements and/or steps are comprised or are to be performed in any particular embodiment.

It should be emphasized that the above-described examples are merely possible examples of implementations and set forth for a clear understanding of the present disclosure. Many variations and modifications may be made to the above-described examples without departing substantially from the spirit and principles of the present disclosure. Further, the scope of the present disclosure is intended to cover any and all appropriate combinations and sub-combinations of all elements, features, and aspects discussed above. All such appropriate modifications and variations are intended to be included within the scope of the present disclosure, and all possible claims to individual aspects or combinations of elements or steps are intended to be supported by the present disclosure.

What is claimed is:

1. An apparatus comprising:
   a sensor array disposed in a fluid distribution system, the sensor array comprising a pressure sensor, a temperature sensor, a turbidity sensor, a pH sensor, and a chlorine sensor;
   a monitoring device comprising
      an antenna contained within a first housing section,
      a power source contained within a second housing section, the second housing section defining a lower end and an opposed upper end removably attached to the first housing section, and
      a parameter sensing portion configured to receive an electronic signal from at least one sensor in the sensor array and to monitor a parameter of the fluid distribution system sensed by the at least one sensor, the parameter sensing portion comprising a printed circuit board and a plurality of sensor ports mounted to the printed circuit board, one sensor port per each sensor in the sensor array, and a service port configured to connect to a service device, the printed circuit board contained within a third housing section, the third housing section removably attached at a proximal end to the lower end of the second housing section; and
   a computing system communicating with the monitoring device, the computing system configured to detect a second sensor in the fluid distribution system;
   wherein the first housing section, the second housing section, and the third housing section each define a separate module that as removably attached together form a case configured for modular disassembly;
   wherein the third housing section defines a distal end opposite the proximal end, and a recessed surface through which each sensor port in the plurality of sensor ports protrudes, the recessed surface recessed with respect to the distal end.

2. The apparatus of claim 1, further comprising an auxiliary power input operably connected to the power source.

3. The apparatus of claim 2, wherein the auxiliary power input comprises a waterproof connector attached to a top of the monitoring device.

4. The apparatus of claim 2, wherein the auxiliary power input is mounted on a planar upper surface of the first housing section.

5. The apparatus of claim 2, wherein the auxiliary power input is connected by a wire to the power source in the second housing section.

6. The apparatus of claim 2, wherein the auxiliary power input is configured to connect to an external power source to recharge the power source in the second housing section.

7. The apparatus of claim 1, further comprising a telescopic enclosure housing the monitoring device, the telescopic enclosure extending from a top of a pipe in the fluid distribution system to a ground level.

8. The apparatus of claim 1, wherein the parameter sensing portion is further configured to operate a solenoid to cause a flushing operation to be performed in the fluid distribution system.

9. The apparatus of claim 1, wherein the monitoring device is installed in a pit in a roadway.

10. The apparatus of claim 1, wherein the circuit board is encased in potting material.

11. The apparatus of claim 1, wherein the power source is a battery pack encased in potting material.

12. The apparatus of claim 1, wherein the first housing section defines a contact surface;
   wherein the second housing section defines a lower end and an opposed first flange;
   wherein the contact surface and the first flange are configured to receive a first fastener, the first fastener configured to removably attach the second housing section to the first housing section;
   wherein the third housing section defines a second flange; and
   wherein the lower end of the second housing section and the second flange of the third housing section are configured to receive a second fastener, the second fastener configured to removably attach the third housing section to the second housing section.

13. The apparatus of claim 12, wherein the first fastener is a first screw and the second fastener is a second screw.

14. The apparatus of claim 12, wherein the first housing section defines a cavity, and wherein the first flange of the second housing section is received in the cavity.

15. A monitoring device configured to connect to a sensor array disposed in a fluid distribution system, the sensor array comprising a pressure sensor, a temperature sensor, a turbidity sensor, a pH sensor, and a chlorine sensor, the monitoring device comprising:
   an antenna contained within a first housing section;
   a power source contained within a second housing section, the second housing section defining a lower end and an opposed upper end removably attached to the first housing section;
   a solenoid; and
   a parameter sensing portion configured to monitor a pressure parameter, a temperature parameter, a turbidity parameter, a pH parameter, and a chlorine parameter of a fluid distribution system, the parameter sensing portion comprising a printed circuit board and a plurality of sensor ports mounted to the printed circuit board, one sensor port per each sensor in the sensor array, and a service port configured to connect to a service device, the parameter sensing portion further configured to operate the solenoid to cause a flushing operation to be performed in the fluid distribution system when a parameter condition is triggered, the parameter sensing portion printed circuit board contained within a third housing section, the third housing section removably attached at a proximal end to the lower end of the second housing section;

wherein the first housing section, the second housing section, and the third housing section each define a separate module that as removably attached together form a case configured for modular disassembly;

wherein the third housing section defines a distal end opposite the proximal end, and a recessed surface through which each sensor port in the plurality of sensor ports protrudes, the recessed surface recessed with respect to the distal end.

16. A system for sensing parameters in a fluid distribution system, the system comprising:

a monitoring device configured to connect to a sensor array disposed in the fluid distribution system, the sensor array comprising a pressure sensor, a temperature sensor, a turbidity sensor, a pH sensor, and a chlorine sensor, the monitoring device, the monitoring device comprising an antenna contained within a first housing section,
- a power source contained within a second housing section, the second housing section defining a lower end and an opposed upper end removably attached to the first housing section, and
- a parameter sensing module configured to receive an electronic signal from at least one sensor in the sensor array and to monitor a parameter of the fluid distribution system sensed by the at least one sensor, the parameter sensing module comprising a printed circuit board and a plurality of sensor ports mounted to the printed circuit board, one sensor port per each sensor in the sensor array, and a service port configured to connect to a service device, the printed circuit board contained within a third housing section, the third housing section removably attached at a proximal end to the lower end of the second housing section; and
- a computing system comprising a processing resource and a non-transitory computer-readable storage medium, the computing system configured to
  receive configuration data defining a configuration profile for the monitoring device, the configuration profile relating to a parameter configuration of the monitoring device,
  communicate the configuration data to the monitoring device, and
  detect a second sensor in the fluid distribution system;

wherein the first housing section, the second housing section, and the third housing section each define a separate module that as removably attached together form a case configured for modular disassembly;

wherein the third housing section defines a distal end opposite the proximal end, and a recessed surface through which each sensor port in the plurality of sensor ports protrudes, the recessed surface recessed with respect to the distal end.

17. The system of claim 16, further comprising a telescopic enclosure housing the monitoring device, the telescopic enclosure extending from a top of a pipe in the fluid distribution system to a ground level.

18. The system of claim 16, wherein the parameter sensing module is further configured to operate a solenoid to cause a flushing operation to be performed in the fluid distribution system.

19. The system of claim 16, wherein the first housing section defines a contact surface;

wherein the second housing section defines a lower end and an opposed first flange;

wherein the contact surface and the first flange are configured to receive a first fastener, the first fastener configured to removably attach the second housing section to the first housing section;

wherein the third housing section defines a second flange; and wherein the lower end of the second housing section and the second flange of the third housing section are configured to receive a second fastener, the second fastener configured to removably attach the third housing section to the second housing section.

* * * * *